(12) United States Patent
Levy et al.

(10) Patent No.: US 7,569,392 B2
(45) Date of Patent: Aug. 4, 2009

(54) MULTIPLEX SPATIAL PROFILING OF GENE EXPRESSION

(75) Inventors: Shawn Levy, Hendersonville, TN (US); Richard M. Caprioli, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 515 days.

(21) Appl. No.: 11/031,973

(22) Filed: Jan. 7, 2005

(65) Prior Publication Data

US 2005/0196786 A1 Sep. 8, 2005

Related U.S. Application Data

(60) Provisional application No. 60/535,075, filed on Jan. 8, 2004.

(51) Int. Cl.
| | |
|---|---|
| C12Q 1/68 | (2006.01) |
| G01N 33/53 | (2006.01) |
| C07H 21/02 | (2006.01) |
| C07H 21/04 | (2006.01) |
| C07K 16/00 | (2006.01) |
| C07K 2/00 | (2006.01) |
| C12N 15/11 | (2006.01) |
| C07K 17/02 | (2006.01) |

(52) U.S. Cl. ............... 436/6; 435/7.1; 530/387.1; 530/350; 530/324; 536/23.1

(58) Field of Classification Search .......... None
See application file for complete search history.

(56) References Cited

U.S. PATENT DOCUMENTS

| 6,027,890 A | 2/2000 | Ness et al. ............... 435/6 |
| 2002/0042112 A1* | 4/2002 | Koster et al. ............. 435/174 |
| 2002/0192676 A1* | 12/2002 | Madonna et al. .......... 435/6 |

FOREIGN PATENT DOCUMENTS

| WO | WO 01/15737 | 3/2001 |
| WO | WO 02/18644 | 3/2002 |
| WO | WO 02/080649 | 10/2002 |
| WO | WO 02/097703 | 12/2002 |
| WO | WO 03/008547 | 1/2003 |

OTHER PUBLICATIONS

Caprioli et al., "Molecular imaging of biological samples: localization of peptides and proteins using MALDI-TOF MS," *Anal Chem*, 69:4751-4760, 1997.
Gygi et al., "Quantitative analysis of complex protein mixtures using isotope-coded affinity tags," *Nat Biotechnol*, 17:994-999, 1999.
Han et al., "Quantitative profiling of differentiation-induced microsomal proteins using isotope-coded affinity tags and mass spectrometry," *Nat Biotechnol*, 19:946-951, 2001.
Koomen et al., "Mapping of surrogate markers of cellular components and structures using laser desporption/ionization mass spectrometry," *J Mass Spectrom*, 35:258-264, 2000.
Onnerfjord et al., "Homogenous sample preparation for automated high throughput analysis with matrix-assisted laser desorption/ionisation time-of-flight mass spectrometry," *Rapid Commun Mass Spectrom*, 13:315-322, 1999.
Rubakhin et al., "Characterization of the Aplysia californica cerebral ganglion F cluster," *J Neurophysiol*, 81:1251-1260, 1999.
Stetsenko and Gait, "Efficient conjugation of peptides to oligonucleotides by 'native ligation,'" *J Org Chem*, 65:4900-4908, 2000.
Todd et al., "Organic ion imaging of biological tissue with secondary ion mass spectrometry and matrix-assisted laser desorption/ionization," *J Mass Spectrom*, 36:355-369, 2001.
Zhou et al., "Quantitative proteome analysis by solid-phase isotope tagging and mass spectrometry," *Nat Biotechnol*, 20:512-515, 2002.

* cited by examiner

*Primary Examiner*—James Martinell
(74) *Attorney, Agent, or Firm*—Fulbright & Jaworski, LLP

(57) ABSTRACT

The present invention provides mass tag complexes that permit simultaneously obtaining information of a plurality of biological molecules. The biological molecules may be RNA or protein, and the information includes both level of expression as well as spatial disposition within a cell or tissue. The mass tag comprise a core structure, a target binding structure (e.g., nucleic acid or peptide binding structure), a cleavable linker and a mass tag that exhibits a unique mass spectroscopy signal.

40 Claims, 4 Drawing Sheets

FIG. 1A-C

FIGS. 4A-B
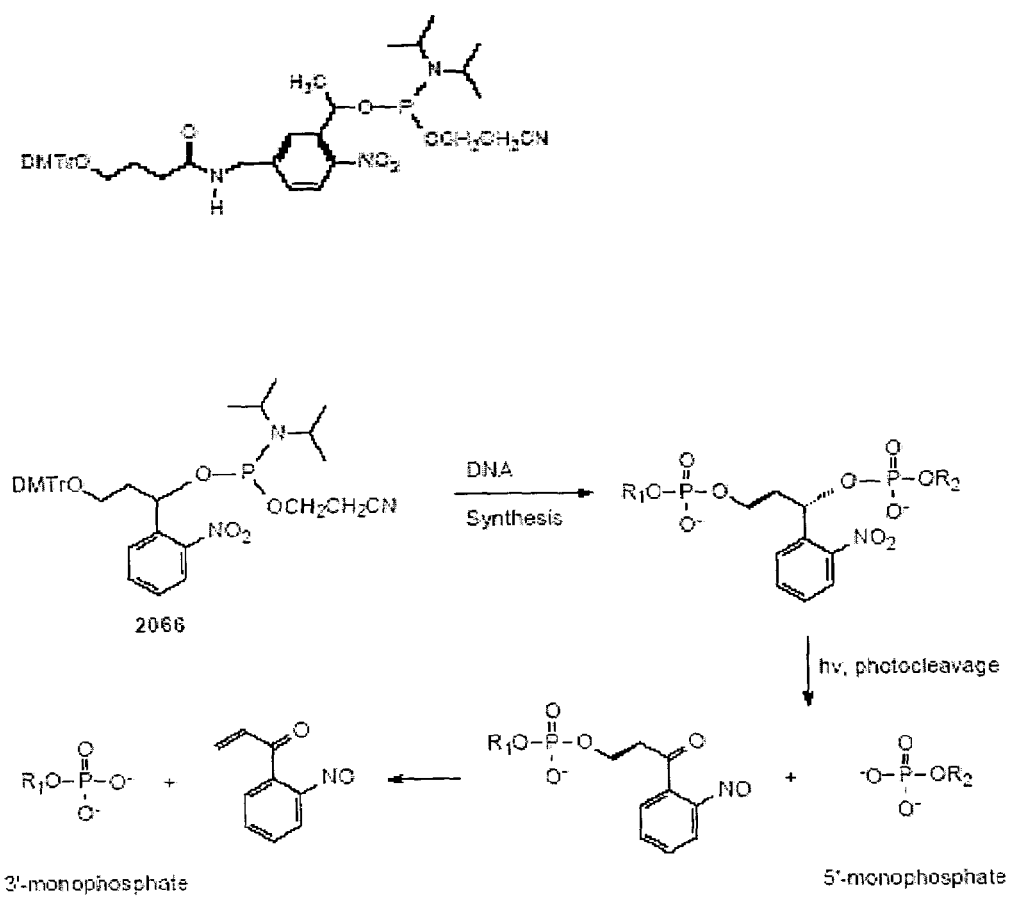

MULTIPLEX SPATIAL PROFILING OF GENE EXPRESSION

The present application claims benefit of priority to U.S. Provisional Application Ser. No. 60/535,075, filed Jan. 8, 2004, the entire contents of which are hereby incorporated by reference.

BACKGROUND OF THE INVENTION

1. Field of the Invention

The present invention relates generally to the field of molecular biology. More particularly, it relates to the use of mass tag complexes to permit simultaneously obtaining of gene expression information on a plurality of targets. In addition, it permits one to perform spatial profiling, i.e., securing information on both expression level and cellular position.

2. Description of Related Art

Localization of specific messenger RNA (mRNA) and protein molecules within cells and tissues can provide important information on differential expression and help elucidate mechanisms of pathophysiologic changes. The most widely used techniques for assessing the cellular and tissue distribution of protein and mRNA are immunohistochemistry and in situ hybridization, respectively. In the clinical setting, immunohistochemistry is an established technique in modern cancer biology and oncology and many diagnoses are based on its findings. Since these techniques are used with sectioned tissues, the spatial and cellular resolution that is present in the whole organ or tumor is maintained. Although this allows a level of cellular resolution that is not possible with methodologies that require cell disruption or homogenization, a major limitation is that the number of transcripts that can be simultaneously detected is small. Generally, a single transcript of interest is probed in a tissue section with multiple, adjacent sections being used to detect larger numbers of transcripts in parallel assays.

In contrast, the wealth of genomic information from the genome sequencing projects combined with the development of high-density profiling technologies such as DNA microarrays now allows simultaneous profiling of tens of thousands of transcripts. The efficiency in the number of transcripts that can be simultaneously profiled is unparalleled compared to any other technique, however there are other limitations associated with microarray technologies. DNA microarrays are not suitable for in-situ assays and therefore do not allow spatial and cellular orientations of the profiled transcripts to be observed. Furthermore, the amount of RNA material that is required for a single microarray assay is quite large compared to the amount of RNA present in a single cell. Methods for isolating single cells or small groups of cells using laser capture microdissection followed by RNA amplification techniques have helped with this limitation, but efficiency is severely impacted and the use of microarrays to profile a significant number of individual cells or small groups of cells becomes impractical.

Recently, several reports have described the use of tag molecules to specifically label a population of proteins to allow a comparative analysis of two complex protein mixtures (Zhou et al., 2002; Han et al., 2001; Gygi et al., 1999). These tag molecules are identical in chemical structure, but differ in total mass. A "heavy" version of the tag contains deuterium, while the "light" version contains hydrogen, providing a difference in total mass based on the number of deuterium versus hydrogen atoms present. The remaining structure contains a reactive group to facilitate binding to proteins and an affinity tag, such as biotin. Together, these tags are referred to as isotope-coded affinity tags (ICAT). By labeling two complex protein mixtures isolated from two cell states with a heavy and light ICAT tag, respectively, the states can be differentially analyzed. Following labeling, the mixtures are combined, fractionated and analyzed by liquid chromatography-mass spectrometry (LC-MS). The same protein from each population can be identified, and a relative ratio between the same protein from the different cell states established based on the presence of the heavy or light affinity tag. A variation on this theme was recently described that adopts that ICAT method to the solid phase to increase the efficiency and reproducibility in the automation of the process. A similar isotope tag is coupled to a solid bead by a photocleavable linkage, which provides an efficient mechanism for the purification of the captured proteins or peptides followed by photocleavage away from the beads and analysis by LC-MS (Zhou et al., 2002).

Thus, there remains a need to develop technologies that allow the efficient and spatial profiling of a moderate number of genes from intact tissue specimens.

SUMMARY OF THE INVENTION

In accordance with the present invention, there is provided a mass tag complex comprising (i) a core structure; (ii) a target binding agent; (iii) a mass unit that permits detection by mass spectroscopy; and (iv) a cleavage site operably connected to said mass unit. The complex may further comprise a spacer unit operably connected to said cleavage site and/or said target binding agent. The cleavage site may be photocleaved, chemically cleaved or enzymatically cleaved. The mass unit may be a peptide. The target binding agent may be an oligonucleotide that hybridizes to an RNA of interest, for example, of about 8 to about 25 nucleotides in length. Alternatively, the target binding agent may be an antibody that binds to a protein of interest, such as an Ig, F(ab), F(ab')$_2$ or single chain antibody. The core structure is a polar-neutral, water-soluble structure with a minimum molecular weight that permits linking of mass unit and the target binding agent through cleavable linkages. The target binding agent and said mass unit may be independently linked to said core structure.

In another embodiment, there is provided a population of mass tag complexes, each complex comprising (i) an identical core structure; (ii) a target binding agent with a distinct target specificity; (iii) a distinct mass unit that permits detection by mass spectroscopy; and (iv) a cleavage site operably connected to said mass unit. Each complex may further comprise a spacer unit operably connected to said each of cleavage sites and/or said target binding agents. Each of said mass units may be a peptide. The cleavage sites may be photocleaved, enzymatically cleaved or chemically cleaved. Each of said target binding agents may be an oligonucleotide, each of which hybridizes to a distinct RNA of interest, for example, one of about 8 to about 25 nucleotides in length. The target binding agents may be antibodies that bind to different proteins of interest, such as Igs, F(ab)s, F(ab')$_2$s or single chain antibodies. Each of the core structures are polar-neutral, water-soluble structures with a minimum molecular weight that permits linking of mass unit and the target binding agent through cleavable linkages. Each of said target binding agents and said mass units may be independently linked to said core structure.

In yet another embodiment, there is provided a method of simultaneously obtaining information on a plurality of distinct biomolecules comprising (a) providing a population of mass tag complexes, each complex comprising (i) an identical core structure, (ii) a target binding agent with a distinct target specificity, (iii) a distinct mass unit that permits detection by mass spectroscopy, and (iv) a cleavage site operably connected to said mass unit; (b) contacting said population with a biomolecule-containing sample; (c) cleaving said cleavage site; and (d) subjecting said sample to mass spectroscopy. The mass spectroscopy may be MALDI-TOF.

The method may further comprise a step, between steps (b) and (c), of spatially fixing said biomolecules and target binding agents. The biomolecules and target binding agents may be located in a cell, which may be comprised within an intact tissue specimen or organism. The mass unit may be a peptide. The cleavage site may be photocleaved, and step (c) may comprise subjecting said sample to an appropriate light source. The target binding agent may be an oligonucleotide that hybridizes to an RNA of interest, for example, of about 8 to about 25 nucleotides in length. The target binding agent may be an antibody that binds to a protein of interest, such as an Ig, F(ab), $F(ab')_2$ or single chain antibody. The core structure is a polar-neutral, water-soluble structure with a minimum molecular weight that permits linking of mass unit and the target binding agent through cleavable linkages. The cell may be from a patient with a pathologic condition, such as cancer, an inflammatory disease, an infection, or a developmental disease. The patient may have been treated with a therapy.

In still yet another embodiment, there is provided a method of obtaining information on the spatial position of a biomolecule in a cell comprising (a) providing a mass tag complex comprising (i) a core structure, (ii) a target binding agent, (iii) a mass unit that permits detection by mass spectroscopy, and (iv) a cleavage site operably connected to said mass unit; (b) contacting said mass tag complex with a cell-containing sample; (c) spatially fixing said biomolecule and target binding agent; (d) cleaving said cleavage site; and (e) subjecting said sample to mass spectroscopy. The method may further comprise obtaining information on the expression level of said biomolecule, or further comprise obtaining information on a plurality of distinct biomolecules by providing a population of mass tag complexes, each complex comprising an identical core structure; a target binding agent with a distinct target specificity; a distinct mass unit that permits detection by mass spectroscopy; and a cleavage site operably connected to said mass unit. The biomolecule may be an RNA or a protein. The cell may be located in an intact tissue specimen or an organism.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Fresh-frozen liver section-no treatment. (FIG. 1B) Fresh frozen liver section fixed with ethanol. (FIG. 1C) Fresh frozen liver section treated with water for 3 minutes.

FIGS. 4A-B—(FIG. 4A) Structure of PC Spacer Phosphoramidite Photocleavable Linker. (FIG. 4B) Photocleavage using PC Linker Phosphoramidite.R1 represents the peptide, PMR conjugate. R2 represents the cleaved oligonucleotide.

DESCRIPTION OF ILLUSTRATIVE EMBODIMENTS

Figure 1:
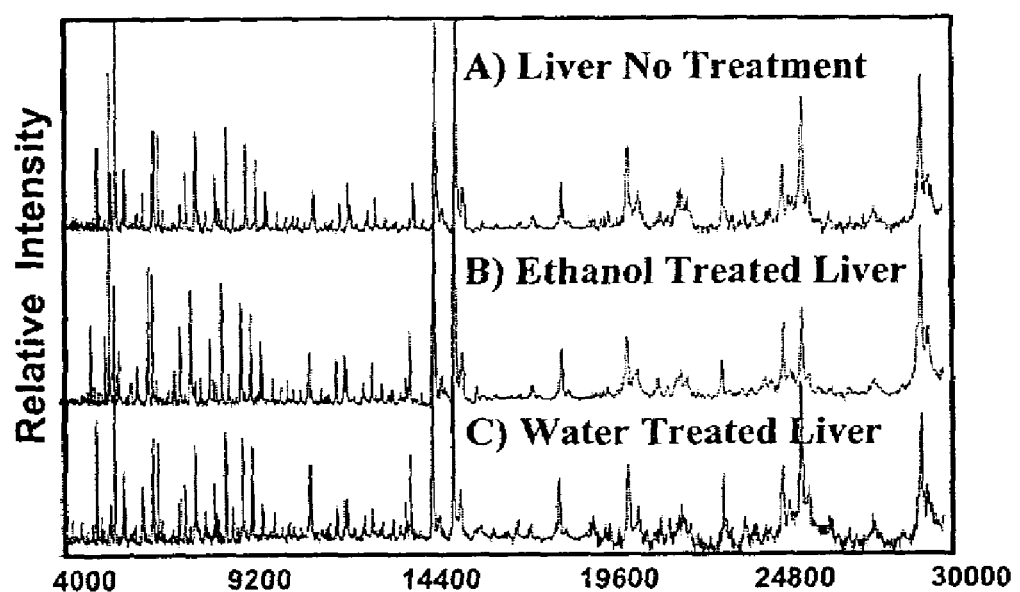
FIGS. 1A-C—Ethanol treatment of tissue sections does not significantly change IMS spectra.

The technologies employed for the global profiling of gene expression at the RNA and protein levels have generally followed separate technology paths. Over the last several years, DNA microarrays containing probes representing a significant portion of human transcripts have been useful in defining distinct patterns of gene expression among subsets of related tumors. Similar to genomic techniques, but utilizing separate technological platforms, protein profiling technologies allow the determination of changes in protein expression patterns resulting from transcriptional regulation with the additional capabilities of monitoring changes due to post-transcriptional control, post-translational modifications and changes in cellular localization. Given that global expression profiles obtained using genomic technologies as well as proteomic technologies are highly complementary, a combined approach to RNA and protein profiling may well uncover expression patterns that could not be appreciated using any single approach.

One area in which global expression profiling has seen significant application is in the examination of cancer and normal tissues. Analyses of gene expression at the transcriptional and proteomic levels have been particular useful in describing distinct patterns of gene expression among subsets of related tumors. Although high-density expression profiling by microarray, which allows tens of thousands of genes to be profiled simultaneously, has become a widely adopted technology for the study of human cancer and related model systems, the amount of biological material required for each assay is significant. Additionally, identifying spatial gene expression patterns in complex tissues or tumors is extremely inefficient, i.e., next to impossible.

Traditional in situ hybridization methods utilize radioactive, fluorescent, chemiluminescent, enzymatic or chemical colormetric detection mechanisms to visualize the hybridization of a probe sequence to a mRNA transcript, or an antibody to a protein, either of which may be present in the tissue section or cells being interrogated. Although well established and efficient, the main limitation of these detection methods is the number of distinct oligonucleotides that can be detected. Even with fluorescent detection, only a small number (two to four by most accounts) of molecules can be simultaneously visualized. However, the spatial resolution of the in situ process remains superior to methods that require disruption of the tissue or cells of interest. The present invention overcomes these limitations by employing novel mass tag complexes that permit the simultaneous obtaining of expression information on a large number of target molecule, including both amount and location of expression.

I. Mass Tag Complexes

A. Nucleic Acid Targets

Using the basic premise of the ICAT technology, described in the Background, the present invention provides tag mass complexes that can be used in in situ hybridization reactions, followed by detection and visualization by Imaging Mass Spectroscopy (IMS), using Matrix-Assisted Laser Desorption Ioniozation Time of Flight Mass Spectroscopy (MADLI-TOF MS). The mass tags are linked to an oligonucleotide through a photocleavable linker. The photocleavable linkage is used to separate the specific mass tag away from the oligonucleotide. Since IMS can detect very small mass changes in the tag molecules (as illustrated by the use of deuterium-labeled ICAT tags (Gygi et al., 1999), coupling specific mass tags with different oligonucleotide sequences will allow the simultaneous detection of several mass tags from the same tissue section, which is a tremendous advance compared to standard in situ techniques.

B. Protein Targets

Using an approach almost identical to that discussed above for nucleic acids, the present invention also provides tag molecules that can be used in in situ for the detection and visualization, by MADLI-TOF MS, of proteins. Tags are linked to an antibody through the photocleavable linker. The photocleavable linkage is used to separate the very specific mass tag away from the antibody. Coupling specific mass tags with different antibodies will allow the simultaneous detection of several mass tags from the same tissue section.

C. Mass Unit

The mass tag unit can be any non-reactive, polar-neutral, water-soluble structure with a specific mass range of 900-2000 AMUs with efficient ionization using standard MS or MS-MS techniques. In one embodiment, the diversity of mass tags will be provided by the use of short peptides coupled to the target binding agent through a linker. Small peptides are easy to synthesize and have enough structural diversity so that the individual members of a probe library could each have a unique peptide-based MS tag. Ideally, the mass of the tag should be greater than 900 to insure that the MALDI matrix or other ionizable species do not interfere with the IMS analysis. This would require peptides between four and six amino acids long. Standard solution-phase peptide synthesis will be used for the preparation of the tag with the N-terminus protected as an FMOC and the C-terminus as a benzyl ester. The choice of amino acids for mass tags will be restricted to polar neutral amino acids for nucleic acid targets and binding agents since highly charged amino acids tags may form secondary structure with the probe DNA sequence through ion pairing interactions and thus interfere with hybridization to a target RNA. Using predominately polar amino acid residues will also ensure high water solubility. A six amino acid peptide tag incorporating only 6 standard, neutral, polar amino acids (Ser, Thr, Cys, Asn, Gln, and Tyr) would provide up to 46,656 different tag molecules.

Because standard MALDI-TOF MS will be used in the IMS, peptides with different sequences but the same mass will be indistinguishable. A small program has been developed using the software package Mathmatica to generate all unique mass tags possible from a user-defined set of parameters including peptide length, amino acid identity and mass. However, tandem MS-MS instrumentation that is able to distinguish mass tags with the same mass, but different peptide sequences, based on fragmentation in the second MS sector is available in IMS, but is not as mature as the MALDI-TOF instrument currently in use. Future use of tandem MS is contemplated as the diversity of mass tags useful in MALDI-TOF IMS may eventually be exhausted.

D. Cleavage Sites

Another element of the mass tag complex is a cleavage site. This site permits one to release the mass unit from the complex during detection. In so doing, the resolution and signal-to-noise of the overall system is dramatically improved. A variety of cleavages sites may be employed, including photocleavable, chemically cleaved and enzymatically cleaved sites.

E. Core and Synthetic Schemes

The core structure is a multifunctional linking unit. Requirements are minimal, but the core must provide a cleavable linkage between a MS detection molecule (short peptide sequence in the case of this invention) and a biological detection molecule (nucleotide sequence for the detection of specific RNA and DNA species of interest; antibody molecule for the detection of both individual peptides or proteins as well as complexes of peptides or proteins of interest; discussed below) through a cleavable linker. Another requirement is that the core must not interfere with the binding of the biological detection molecule through ionic or steric interference. Otherwise, the exact structure is not critical.

The design criteria for the DNA probe with mass spectrometric tags is described below. Hybridization probes will be synthesized by standard solid-phase oligonucleotide synthesis using phosphoramidite reagents. Thus, the reagent for incorporation of the MS tag must be compatible with standard DNA synthesis technology.

Peptide tags (discussed above) may be utilized for MS detection. Small peptides are easy to synthesize and have enough structural diversity so that the individual members of a probe DNA library could have a unique peptide-based MS tag. Ideally, the mass of the tag should be in the range of 1000 AMUs to insure that the MALDI matrix does not interfere with the analysis and identification of the specific peptide tag. Therefore, peptides between four and six amino acids long are preferred.

Overview of Oligonucleotide-Peptide Conjugation (OpeC™) Technology. OpeC™ technology allows the convenient conjugation of peptides to oligonucleotides in three steps using three main reagents: an Oligonucleotide Modifying Reagent (OMR); a Peptide Modifying Reagent (PMR); and a Conjugation Reagent. The OpeC™ technology is based on the principle of template-free "native ligation" and was developed by Michael Gait at the Medical Research Council in Cambridge, UK (Patent No. PCT/GB00/03306 and described in Stetsenko, 2000. The OpeC™ technology is now a commercial product of Link Technologies, Lanarkshire, Scotland.

To facilitate the efficient coupling of oligonucleotides to peptides, the basic steps followed in the process are synthesis of oligonucleotides and peptides by standard means followed by the modification of each of the synthesized components by their respective reagent. Following purification, the two components are coupled in a reaction using the third reagent. Specifically, the Oligonucleotide Modifying Reagent is used in the final coupling step in standard phosphoramidite controlled-pore glass solid-support oligonucleotide assembly. A coupling time of 10 minutes on a 1 μmol scale results in an average yield of >97% as measured by HPLC. Conventional deprotection with an aqueous ammonia solution at 55° C. generates the functionalized oligonucleotide in solution, maintaining the S-tert-butylsulfenyl protecting group but removing the $N_a$-Fmoc group. Addition of the OMR results in a 368.45 mass unit increase in the weight of the oligonucleotide.

The Peptide Modifying Reagent is added after the final coupling step of standard Fmoc-based solid-phase peptide assembly, but before removing the peptide from the solid support. Use of a PEG-polystyrene support containing a standard Rink amide linker or PAL linker protects the C-terminus of the peptide from possible interference with native ligation. The modified peptide is released from the solid support as a C-terminal amide. This occurs during side-chain deprotection by treatment with trifluoroacetic acid-phenol-benzylmercaptan-water. Addition of the PMR results in a 206.27 mass unit increase in the weight of the peptide.

Conjugation of the modified oligonucleotide with the modified peptide is based on the "native ligation" of an N-terminal thioester-functionalised peptide to a 5'-cysteinyl oligonucleotide. The Conjugation Reagent removes the tert-butylsulfenyl protecting groups, using thiophenol and benzyl mercaptan as conjugation enhancers.

Photo-cleavable Modification Reagents. Because this invention requires the ultimate release of the peptide from the coupled oligonucleotide when exposed to the ionizing laser of the mass spectrometry instrument, a photocleavable linker is included during the last step of the oligonucleotide synthesis prior to addition of the OMR. The photocleavable linker that was used here was developed by Kenneth Rothschild at Ambergen Inc, Boston, Mass. Described in (Olejnik, 1999). The general design of Ambergen's photo-cleavable (PC) monomers is based on an α-substituted 2-nitrobenzyl group. The photo-reactive group originates from a cyanoethyl phosphoramidite for use in standard automated DNA synthesizers. The PC spacer phosphoramidite, unlike other 5'-terminus PC modifiers, can be used during an intermediate step of oligonucleotide synthesis, a vital component of this technology as it allows the efficient use of the OMR following addition of the cleavable linker (FIG. 1A). The nature of the conjugation reaction requires that the OMR be in a terminal position, therefore situating the PC spacer between the OMR and the oligonucleotide suits our purpose ideally. Photocleavage of the final conjugate results in the oligonucleotide bound to a single phosphate group and the peptide attached to the PMR, the OMR, and the phosphoramidite spacer (FIG. 1B). For a list of component weights see Table 1.

Preparation of Modified Oligonucleotide. Oligonucleotides as assembled using the standard 2-cyanoethyl phosphoramidite method on a standard glass support. As mentioned previously, the PC Spacer Phosphoramidite is added to the 5' end of the last nucleotide during synthesis. After removal of the last dimethoxytrityl group, the OMR is coupled (150 μmol in 1 ml dry acetonitrile to give a 0.15 M solution) to the support-bound oligonucleotide using the extended coupling protocol. Following normal iodine-water oxidation, the support is flushed with 20% piperidine in DMF for 10 min, washed with 10 ml of DMF, 10 ml of acetonitrile, then dried. The oligonucleotide is cleaved from the solid support by treating with 0.5 ml of aqueous ammonia at room temperature for two hours. The product is washed with an additional 0.5 ml of concentrated ammonia then transferred to a screw-capped polypropylene tube and heated for 16 hr at 55° C. This step ensures complete deprotection of the oligonucleotide at the nucleobase and phosphate residues. Following cooling and evaporation, 1 ml of deionized water is added and evaporated to dryness under vacuum.

Preparation of Modified Peptide. The choice of amino acids for the tag will be restricted to polar neutral amino acids. There is concern that highly charged amino acids tag may form secondary structures with the probe DNA sequence through ion pairing interactions, and thus interfere with hybridization to a target RNA. Thus, one will use predominately polar amino acid residues to ensure high water solubility. A large number of natural and unnatural amino acids are available and should provide enough diversity for this encoded tagging of the probe DNA. The peptide tag will have a free N-terminus that will be the charged moiety of the mass spectral detection. In addition, one should be able to readily incorporate a brominated amino acid, such a 3-bromotyrosine which will provide a unique signature in the mass spectrum and thus enhance detection. Alternatively, metal ions may also be incorporated into the chemical structure to eliminate the need for matrix material to facilitate efficient ablation during MS. This would potentially increase resolution and decrease any detection variability introduced by the matrix material.

Synthesis is generally performed on a 0.1 mmol scale using a standard Fmoc protocol and a PAL-PEG-PS solid support. After removing the last $N_a$-Fmoc, the PMR is coupled to the last amino acid of the support bound peptide (using 4.5 equivalents of PMR and 1 equivalent of HOBt in 2 ml DMF) for 4 hr at room temperature. The resin is washed with 5×5 ml DMF, 3×5 ml methanol, 2×5 ml diethyl ether, and dried. The modified peptide is cleaved from the solid support and sidechains deprotected by treating with TFA-benzylmercaptan-phenol-water (90:5:2.5:2.5 v/v/w/v) for 1-6 hrs depending on $N^G$-2,2,4,6,7-pentamethyldihydrobenzofuran-5-sulfonyl (Pbf) arginine content. TFA is removed by flushing the filtrate with a stream of nitrogen. Precipitation is then done with cold (−20° C.) diethyl ether followed by washing three times with diethyl ether and drying under vacuum to remove all traces of TFA. Before use, the modified peptide is purified using any standard peptide purification technique.

Preparation of Oligonucleotide-Peptide Conjugate. The Conjugation Reagent is prepared by dissolving the dry form of the reagent in 3.5 ml 0.1 M ammonium acetate and adding 5 M NaOH to a pH of approximately 7.5. To 1 μmol modified oligonucleotide pellet is added 1 ml of the Conjugation Reagent and incubated at room temperature for 3 hrs. Five molar equivalents of modified peptide with respect to modified oligo is dissolved in 200 μl 0.5 M ammonium bicarbonate and 300 μl HPLC grade acetonitrile. 500 μl of the pre-reduced oligonucleotide solution is added along with 1% v/v thiophenol and 2% v/v benzyl mercaptan to the reaction followed by thorough mixing and incubation at 37° C. for 24 hrs. Thiophenol is removed from the reaction by washing with 5×0.5 ml pentane. Traces of pentane are removed by evaporation under vacuum. The conjugation reaction is further purified using gel purification or gel filtration prior to use in any hybridization reactions.

TABLE 1

Molecular weights of conjugate components

| Component | Molecular Weight (Da) |
| --- | --- |
| Oligonucleotide | ~23976 |
| Peptide | Variable |
| OMR | 368.45 |
| PMR | 206.27 |
| PC Spacer Phosphoramidite | 784.88 |

Using nearly identical procedures used for the hybridization probes, an encoded tag to be covalently linked to antibodies will be developed using an alternative photocleavable linker that facilitates coupling to amine groups on the antibody of interest. This linker is available from the same sources described above for the hybridization photocleavable linker.

F. Target Binding Agent

1. Nucleic Acids

Certain embodiments of the present invention comprise the preparation and use of a nucleic acid. The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally-occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but specific embodiments will also encompass an additional strand that is partially, substantially or fully complementary to the single-stranded molecule. Thus, a nucleic acid may encompass a double-stranded molecule that comprises one or more complementary strand(s) or "complement(s)" of a particular sequence comprising a molecule. As used herein, a single stranded nucleic acid may be denoted by the prefix "ss," and a double stranded nucleic acid by the prefix "ds."

Nucleobases. As used herein a "nucleobase" refers to a heterocyclic base, such as for example a naturally occurring nucleobase (i.e., an A, T, G, C or U) found in at least one naturally-occurring nucleic acid (i.e., DNA and RNA), and naturally or non-naturally-occurring derivative(s) and analogs of such a nucleobase. A nucleobase generally can form one or more hydrogen bonds ("anneal" or "hybridize") with at least one naturally-occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moiety. Preferred alkyl (e.g., alkyl, carboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-dimethyladenine, an azaadenines, a 8-bromoadenine, a 8-hydroxyadenine, a 6-hydroxyaminopurine, a 6-thiopurine, a 4-(6-aminohexyl/cytosine), and the like. Table 2, showing non-limiting, purine and pyrimidine derivatives, is provided herein below.

TABLE 2

Purine and Pyrmidine Derivatives or Analogs

| Abbr. | Modified base description |
|---|---|
| ac4c | 4-acetylcytidine |
| Chm5u | 5-(carboxyhydroxylmethyl) uridine |
| Cm | 2'-O-methylcytidine |
| Cmnm5s2u | 5-carboxymethylamino-methyl-2-thioridine |
| Cmnm5u | 5-carboxymethylaminomethyluridine |
| D | Dihydrouridine |
| Fm | 2'-O-methylpseudouridine |
| Gal q | Beta,D-galactosylqueosine |
| Gm | 2'-O-methylguanosine |
| I | Inosine |
| I6a | N6-isopentenyladenosine |
| m1a | 1-methyladenosine |
| m1f | 1-methylpseudouridine |
| m1g | 1-methylguanosine |
| m1I | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| Mam5u | 5-methylaminomethyluridine |
| Mam5s2u | 5-methoxyaminomethyl-2-thiouridine |
| Man q | Beta,D-mannosylqueosine |
| Mcm5s2u | 5-methoxycarbonylmethyl-2-thiouridine |
| Mcm5u | 5-methoxycarbonylmethyluridine |
| Mo5u | 5-methoxyuridine |
| Ms2i6a | 2-methylthio-N6-isopentenyladenosine |
| Ms2t6a | N-((9-beta-D-ribofuranosyl-2-methylthiopurine-6-yl)carbamoyl)threonine |
| Mt6a | N-((9-beta-D-ribofuranosylpurine-6-yl)N-methyl-carbamoyl)threonine |
| Mv | Uridine-5-oxyacetic acid methylester |
| o5u | Uridine-5-oxyacetic acid (v) |
| Osyw | Wybutoxosine |
| P | Pseudouridine |
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-((9-beta-D-ribofuranosylpurine-6-yl)carbamoyl)threonine |
| Tm | 2'-O-methyl-5-methyluridine |
| Um | 2'-O-methyluridine |
| Yw | Wybutosine |
| X | 3-(3-amino-3-carboxypropyl)uridine, (acp3)u |

A nucleobase may be comprised in a nucleoside or nucleotide, using any chemical or natural synthesis method described herein or known to one of ordinary skill in the art.

Nucleosides. As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

Nucleotides. As used herein, a "nucleotide" refers to a nucleoside further comprising a "backbone moiety." A backbone moiety generally covalently attaches a nucleotide to another molecule comprising a nucleotide, or to another nucleotide to form a nucleic acid. The "backbone moiety" in naturally-occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally-occurring 5-carbon sugar or phosphorus moiety.

Nucleic Acid Analogs. A nucleic acid may comprise, or be composed entirely of, a derivative or analog of a nucleobase, a nucleobase linker moiety and/or backbone moiety that may be present in a naturally-occurring nucleic acid. As used herein a "derivative" refers to a chemically modified or altered form of a naturally-occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidin rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moiety which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moiety replacing phosphodiester backbone moiety used for improved nuclease resistance, cellular uptake and regulating RNA expression; U.S. Pat. No. 5,858,988 which describes hydrophobic carrier agent attached to the 2'-O position of oligonuceotides to enhanced their membrane permeability and stability; U.S. Pat. No. 5,214,136 which describes olignucleotides conjugaged to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

Polyether and Peptide Nucleic Acids. In certain embodiments, it is contemplated that a nucleic acid comprising a derivative or analog of a nucleoside or nucleotide may be used in the methods and compositions of the invention. A non-limiting example is a "polyether nucleic acid," described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid," also known as a "PNA," "peptide-based nucleic acid analog" or "PENAM", described in U.S. Pat. Nos. 5,786,461, 5891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moiety that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

In certain embodiments, a nucleic acid analogue such as a peptide nucleic acid may be used to inhibit nucleic acid amplification, such as in PCR, to reduce false positives and discriminate between single base mutants, as described in U.S. Pat. No. 5,891,625. In a non-limiting example, U.S. Pat. No. 5,786,461 describes PNAs with amino acid side chains attached to the PNA backbone to enhance solubility of the molecule. Another example is described in U.S. Pat. Nos. 5,766,855, 5,719,262, 5,714,331 and 5,736,336, which describe PNAs comprising naturally- and non-naturally-occurring nucleobases and alkylamine side chains that provide improvements in sequence specificity, solubility and/or binding affinity relative to a naturally occurring nucleic acid.

Preparation of Nucleic Acids. A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266 032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

Purification of Nucleic Acids. A nucleic acid may be purified on polyacrylamide gels, cesium chloride centrifugation gradients, or by any other means known to one of ordinary skill in the art (see for example, Sambrook et al., 2001, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

Nucleic Acid Complements. The present invention also encompasses a nucleic acid that is complementary to a target nucleic acid. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

Hybridization. As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

2. Antibodies

Briefly, an antibody is prepared by immunizing an animal with an immunogen and collecting antisera from that immunized animal. A wide range of animal species can be used for the production of antisera. Typically an animal used for production of anti-antisera is a non-human animal including rabbits, mice, rats, hamsters, pigs or horses. Monoclonal antibodies may be prepared and characterized by standard techniques (see, e.g., Harlow and Lane, 1988; incorporated herein by reference).

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of antibodies varies upon the nature of the immunogen as well as the animal used for immunization. A variety of routes can be used to administer the immunogen (subcutaneous, intramuscular, intradermal, intravenous and intraperitoneal). A second, booster, injection may also be given. The process of boosting and titering is repeated until a suitable titer is achieved. When a desired level of immunogenicity is obtained, the immunized animal can be used to generate mAbs.

MAbs may be readily prepared through use of well-known techniques, such as those exemplified in U.S. Pat. No. 4,196, 265, incorporated herein by reference. Typically, this technique involves immunizing a suitable animal with a selected immunogen composition, e.g., a purified or partially purified PKD protein, polypeptide or peptide or cell expressing high levels of PKD. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

Selected hybridomas are serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

II. MALDI-TOF

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998), peptide and protein analysis (Zaluzec et al., 1995; Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multicomponent quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

A. Sample Preparation

In general, all reasonable efforts should be made to reduce excessive contamination in the samples. Always use the best quality solvents, reagents and samples. HPLC-grade solvents should be the standard in MALDI studies. Keep all samples in plastic containers. Glass containers can cause irreversible sample losses through adsorption on the walls, and release alkali metals into the analyte solution.

Optimum sample handling conditions for biological preparations usually involve non-volatile salts. Desalting might be necessary in the presence of excessive cationization, decreased resolution or signal suppression. Washing the analyte-doped matrix crystals with cold acidic water has been suggested as a very efficient way of desalting samples that have already been crystallized with the matrix. However, whenever possible, it is best to remove the salts, before the crystals are grown, using some of the techniques described later. There is a competition between protonation and cationization in MALDI when salts are present, and the choice between the two processes is still the subject of investigation.

When working with complex biological materials in MALDI it is often necessary to use detergents, otherwise the proteins, specially at <mM concentrations, will be rapidly adsorbed on accessible surfaces. If no detergent is used, agglomeration and adsorption can effectively suppress protein peaks in the spectrum. The effect of detergents on MALDI spectra depends on the type of detergent and sample.

Nonionic detergents (TritonX-100, Triton X-114, N-octylglucoside and Tween 80) do not interfere significantly with sample preparation. In fact, it has even been reported that Triton X-100, in a concentration up to 1%, is compatible with MALDI and in some cases it can improve the quality of spectra. N-octylglucoside has been shown to enhance the MALDI-MS response of the larger peptides in digest mixtures. The addition of nonionic detergents is often a requirement for the analysis of hydrophobic proteins. Common detergents such as PEG and Triton, added during protein extraction from cells and tissues, desorb more efficiently than peptides and proteins and can effectively overwhelm the ion signals. Detergents often provide good internal calibration peaks in the low mass range of the mass spectrum.

Ionic detergents and particularly sodium dodecyl sulfate (SDS), can severely interfere with MALDI even at very low concentrations. Concentrations of SDS above 0.1% must be reduced by sample purification prior to crystallization with the matrix. The seriousness of this effect cannot be ignored given the wide application of MALDI to the analysis of proteins separated by SDS-PAGE. Polyacrylamide gel electrophoresis introduces sodium, potassium and SDS contamination to the sample, and it also reduces the recovered concentration of analyte. Once a protein has been coated with SDS, simply removing the excess SDS from the solution will not improve sample prep for MALDI: the SDS shell must also be removed. Typical purification schemes involve two phase extraction such as reversed-phase chromatography or liquid-liquid extraction. The removal of SDS from protein samples prior to MALDI mass spectrometry is an important issue.

Involatile solvents are often used in protein chemistry. Examples are: glycerol, polyethyleneglycol, β-mercaptoethanol, dimethyl sulfoxide (DMSO) and dimethylformamide (DMF). These solvents interfere with matrix crystallization and coat any crystals that do form with a difficult to remove solvent layer. If you must use these solvents and the dried-droplet method does not yield good results, try a different crystallization technique such as crushed-crystal method.

The use of buffers is often necessary in protein sample preparation to maintain biological activity and integrity. It is generally assumed that MALDI is tolerant of buffers. In cases where buffers are possible sources of interference, a trick that has been shown to work is to increase the matrix:analyte ratio. The effect of six common buffer systems, on the MALDI spectra of bovine insulin, cytochrome c and bovine albumin with DHB as a matrix has been studied (Wilkins et al., 1998).

In order to get "clean samples," free of salts, buffers, detergents and involatile compounds, several experimental approaches have been tested with varying results. A number of researchers have attempted to establish "MALDI from synthetic membranes" as a general purification tool in protein biochemistry. In an extensive series of studies, analyte droplets were deposited on to polymeric membranes (porous polyethylene, polypropylene, analyte, nylon, Nafion, and others), washed in special solvents, and mixed with matrix to provide "clean" crystals. The approach is most useful for the direct analysis of proteins electroblotted from SDS-PAGE gels into synthetic membranes. In a more elaborate study, protein samples were desalted and freed of salts and detergents by constructing self-assembled monolayers of octadecylmercaptan (C18) on a gold coated MALDI probe surface. These surfaces were able to reversibly bind polypeptides through hydrophobic interactions allowing simultaneous concentration and desalting of the analyte.

Surface enhanced affinity capture (SEAC) was created (Hutchens et al., 1993) to facilitate the desorption of specific macromolecules affinity-captured directly from unfractionated biological fluids and extracts, and can also be used as a means for sample purification. Direct analysis of affinity-bound analytes by MALDI TOF is now performed routinely and it is even possible to get customized affinity-capture sample probes from commercial sources.

Purification of analyte samples by traditional methods, such as alcohol or acetone precipitation, HPLC, ultrafiltration, liquid-liquid extraction, dialysis and ion exchange are always recommended; however, the effects of increased sample preparation time and sample recovery yields must be weighed carefully. It is possible to purify samples prior to analysis by using small, commercially available (or even home-made) C18 reverse-phase microcolumns or centrifugal ultrafiltration devices; however, such devices can still suffer from the same drawbacks as large scale separation schemes. Note that acetone precipitation and dialysis usually do not remove enough detergent for MALDI sample preparation.

The degradation of signal intensity and resolution that results from excessive contamination can sometimes be eliminated by more extensive dilution of the protein in the matrix solution, a common trick is to try a 1:5 dilution series of the sample. Diluting the protein solution very often improves the MALDI signal, perhaps by diluting the contaminants while the matrix concentrates the analyte. This trick works well for hydrophobic proteins where the presence of lipids is suspected.

With IMS as the detection mechanism, the ultimate spatial resolution obtainable depends on both the sample preparation and instrument resolution. Most commercial MALDI instruments can obtain resolutions of approximately 25 microns. A recent report by Spengler et al. has described an instrument with resolution in the single micron range (Spengler and Hubert, 2002). Similar to other microscopic techniques, the ultimate resolution achievable depends on the specific sample being analyzed, the tissue preparation techniques and the application of the matrix material. Maintaining the spatial positions of the RNA and proteins during sample processing and detection is particularly important. During matrix application, the peptides and tags in the tissue sample must incorporate into the matrix as it dries and crystallizes. If the matrix dries too quickly, crystal formation and incorporation will be inefficient. If the matrix is too wet, it will cause the proteins and tags to redistribute in the section. Several reports have focused on the development of matrix application techniques and technologies, providing for the optimization of new methods appropriate for the detection of tag molecules in situ (Caprioli et al., 1997; Rubakhin et al., 1999; Todd et al., 2001; Koomen et al., 2000; Onnerfjord et al., 1999).

B. Matrix

Solubility in commonly used protein solvent mixtures is one of the conditions a "good" matrix must meet. Incorporating the protein or peptide (target or standard) into a growing matrix crystal implies that the protein and the matrix must be simultaneously in solution. Therefore, a matrix should dissolve and grow protein-doped crystals in commonly used protein-solvent systems. This condition should be expanded to any solvent system in which the analyte of interest will co-dissolve with the matrix. In practical terms, this means that the matrix must be sufficiently soluble to make 1-100 mM solutions in solvent systems consisting of: acidified water, water-acetonitrile mixtures, water-alcohol mixtures, 70% formic acid, etc.

The light absorption spectrum of the matrix crystals must overlap the frequency of the laser pulse being used. The laser pulse energy must be deposited in the matrix. Unfortunately the absorption coefficients of solid systems are not easily measured and are usually red shifted (Stokes shift) relative to the values in solution. The extent of the shifts varies from compound to compound. The solution absorption coefficients are often used as a guide, and typical ranges for commonly used matrix materials, at the wavelengths they are applied, are $e=3000-16000$ (lmol−1 cm−1). UV-MALDI, with compact and inexpensive nitrogen lasers operating at 337 nm is the most common instrumental option for the routine analysis of peptides and proteins. IR-MALDI of peptides has been demonstrated but is not used in analytical applications. For UV-MALDI, compounds such as some trans-cinnamic acid derivatives and 2,5-dihydroxy benzoic acid have proven to give the best results.

The intrinsic reactivity of the matrix material with the analyte must also be considered. Matrices that covalently modify proteins (or any other analyte) cannot be applied. Oxidizing agents that can react with disulfide bonds and cysteine groups and methionine groups are immediately ruled out. Aldehydes cannot be used because of their reactivity with amino groups.

The matrix material must demonstrate adequate photostability in the presence of the laser pulse illumination. Some matrices become unstable, and react with the peptides, after laser illumination. Nicotinic acid, for example, easily looses; —COOH when photochemically excited leaving a very reactive pyridyl group which results in several pyridyl adduct peaks in the spectrum. This is one of the reasons that the use of nicotinic acid has been replaced by more stable matrices such as SA and CHCA.

The volatility of the matrix material must be contemplated as well. From an instrumental perspective, the matrix crystals must remain in vacuum for extended periods of time without subliming away. Cinnamic acid derivatives perform a lot better in that respect when compared to nicotinic and vanillic acids.

The matrix must have a special affinity for analytes that allows them to be incorporated into the matrix crystals during the drying process. This is undoubtfully the hardest property to quantify and impossible to predict. In the current view of MALDI sample preparation, ion production in the solid-state source depends on the generation of a suitable composite material, consisting of the analyte and the matrix. As the solvent evaporates, the analyte molecules are effectively and selectively extracted from the mother liquor and co-crystallyzed with the matrix molecules. Impurities and other necessary solution additives are naturally excluded from the process.

The matrix molecules must possess the appropriate chemical properties so that analyte molecules can be ionized. Most of the energy from the laser is absorbed by the matrix and results in a rapid expansion from the solid to the gas phase. Ionization of the analyte is believed to occur in the high pressure region just above the irradiated surface and may involve ion-molecule reactions or reaction of excited state species with analyte molecules. Most commonly used matrix materials are organic acids and protonation, the addition of a proton to the analyte molecule to form (M+H)+ ions, is the most common ionization mechanism in MALDI of peptides and proteins. Excited state proton transfer is a plausible mechanism for the charge transfer events that occur in the plume. Compounds, which perform a proton transfer under UV irradiation, are generally usable as matrices for UV-MALDI-MS. Whether the described proton transfer and the resulting metastable excited-state is involved in the ionization process or if it just offers an absorption band in the used wavelength area is not clear.

The final and definitive test for any potential matrix compound is to introduce the material in a laser desorption mass spectrometer and do a MALDI study. Many compounds form protein-doped structures that produce protein ions, but they are disqualified by other factors. The qualities that separate most matrix candidates from the ones that actually work are still very obscure and more studies are needed to improve the understanding of the effects involved.

Once a matrix compound has been proved to deliver ions in a MALDI source, it is also important to look at the performance of the material as far as the extent of matrix adduction to the analyte ions. Matrix adduct ions, (M+matrix+H)+, are usually observed in MALDI spectra; however, extensive adduct formation affects the ability to determine accurate molecular weights when the adductions are not well resolved from the parent peak. The best matrices have low intensity photo chemical adduct peaks.

MALDI is a soft ionization method capable of ionizing very large bioplymers while producing little or no fragmentation. The extent of fragmentation during desorption/ionization must be considered critically during matrix selection. Excessive fragmentation can cause decreased resolution. It is well known that the extent of fragmentation for proteins is strongly related to the matrix compound used. Some matrices are "hotter" than others, leading to more in-source (i.e., prompt) and post-source decay. A good example of a "hot" matrix material is CHCA which produces intense multiply charged ions in the positive ion spectra of proteins and contributes to significant fragmentation in the mass spectrometer.

Even after a matrix has been proved to be useful for a specific peptide or protein there is no algorithm other than trial-and-error to predict its applicability to other sample molecules. More than one matrix material is often required to get a complete representation of a complex mixture.

With a few exceptions, the development of new matrices has relied completely on commercially available compounds. It has been argued that this has limited the ability to effectively correlate matrix structure to MALDI function. More recent efforts (Brown et al., 1997), have tried to overcome this limitation through the intelligent synthesis of compounds that will provide a wide range of functionality. Most fine chemical manufacturers are aware of the utility of some of their compounds as MALDI matrices and have dedicated catalog numbers to those chemicals purified specifically for MALDI application. Matrix compounds are typically used as received from the manufacturer without any prior purification, and it is always a good idea to store them in the dark.

Most MALDI practitioners use MALDI for pure analytical purposes and are not interested in the discovery of novel MALDI materials. Luckily for them, there are a few compounds that provide consistently good results and can be relied upon for the routine analysis of peptides and proteins. S of the most commonly used matrices are a-cyano-4-hydroxycinnamic acid (CHCA), gentisic acid, or 2,5-dihydroxy benzoic acid (DHB), trans-3-indoleacrylic acid (IAA), 3-hydroxypicolinic acid (HPA), 2,4,6-trihydroxyacetophenone (THAP), dithranol (DIT). The definitive choice of matrix material depends on the type of analyte, its molecular weight and the nature of the sample (pure compound, mixture or raw biological extract). In all cases the performance of the matrix material is influenced by the choice of solvent. Experimentation (i.e., trial-and-error laced with a few educated guesses) is generally the only way to find the best sample preparation conditions. Some examples of compounds that have also been used for MALDI of peptides and proteins include: hydroxybenzophenones, mercaptobenthothiazoles, b-carbolines and even high explosives.

Most matrices reported to date are acidic, but basic matrices such as 2-amino-4-methyl-5-nitropyridine and neutral matrices such as 6-aza-2-thiothymine (ATT) are also used, which extends the utility of MALDI to acid sensitive compounds.

Matrix peaks are often used for low mass calibration in the mass axis calibration procedure. [M+Na]+ and [M+K]+ peaks are also observed if samples are not carefully desalted.

1. Matrix Suppression

At appropriate matrix to analyte mixing ratios, small to moderately sized analyte ions (1000-20,000 Da) can fully suppress positively charged matrix ions in MALDI mass spectra. This is true for all matrix species, and is observed regardless of the preferred analyte ion form (protonated or cationized). Since the effect has been observed with a number of matrices including CHCA and DHB, it seems to be a general phenomenon in MALDI. Along with the fact that fragmentation is weak in MALDI, this leads to nearly ideal mass spectra with a strong peak for the analyte ions and no other signals present.

2. Co-Matrices (Matrix Additives)

Several additives have been added to MALDI samples to enhance the quality of the mass spectra. Additives, also known as co-matrices, can serve several different purposes: (1) increase the homogeneity of the matrix/analyte deposit, (2) decrease/increase the amount of fragmentation, (3) decrease the levels of cationization, (4) increase ion yields, (5) increase precision of quantitation, (6) increase sample-to-sample reproducibility, and (7) increase resolution.

The use of co-matrices is much more widespread in the analysis of oligonucleotides, where ammonium salts and organic bases are very common additives. Some MALDI researchers believe that the use of additives may provide the most general and simplest means of improving the current matrix systems. Continuing efforts are needed to evaluate the effects of co-matrices on the MALDI process, and to further characterize additives for such purposes. Some examples of additives used in peptide and protein measurements are: common matrices, bumetanide, glutathione, 4-nitroaniline, vanillin, nitrocellulose and L(-) fucose.

The addition of ammonium salts to the matrix/analyte solution substantially enhances the signal for phosphopeptides. This has been used to allow the identification of phosphopeptides from unfractionated proteolytic digests. The approach works well with CHCA and DHB and with ammonium salts such as diammonium citrate and ammonium acetate.

C. Solvent Selection

Solvent choice remains to this day a trial-and-error process that is governed by the need to maintain analyte solubility and promote the partitioning of the analyte into the matrix crystals during drying of the analyte/matrix solution. As a general rule, it is best to first find the appropriate solvent for the sample.

Once the analyte has been completely dissolved, a solvent should be chosen for the matrix that is miscible with the analyte solvent. In some cases, such as the analysis of peptides and proteins, or oligonucleotides, the appropriate solvents are well known. In the analysis of peptides/proteins 0.1% TFA is the solvent of choice, and for oligonucleotides, pure 18 Ohm water. The matrices for these analytes are dissolved in ACN/0.1% TFA and ACN/$H_2O$, respectively. What follows is a more detailed look at the rules governing the choice of solvents for analyte and matrices in MALDI.

Solubility of the analyte in the solvent system is one of the most important parameters to be considered during solvent selection. The analyte must be truly dissolved in the solvent at all times. Making a slurry of analyte powder and solvent never leads to good results.

Two solvent systems are usually involved in a MALDI sample preparation procedure. There is a solvent system for the analyte sample, and a different solvent for the matrix. In most sample preparation recipes (dried-droplet technique), an aliquot of the matrix solution is mixed with an aliquot of the protein solution to make a crystal-forming mother liquor. Both matrix and analyte solvents must be chosen carefully. It is important that neither the matrix nor the analyte precipitate when the two solutions mix. Particular care must be taken when the analyte's solvent does not contain any organic solvent, which may lead to precipitation of the matrix during mixing. Attention must also be paid to inadvertent changes in solvent composition as caused by selective evaporation of organic solvents from aqueous solutions. Tubes of analyte and matrix solutions should be kept closed while not in use to avoid evaporation.

Analyte solubilization is the key to the successful analysis of hydrophobic proteins and peptides. Owing to their limited solubility in aqueous solvents, alternative solvents for both the matrix and the analyte have been carefully investigated. Several solubilization schemes have been successfully applied including strong organic acids (i.e., formic acid), detergent solutions and non-polar organic solvents. Non-ionic detergents, that improve the solubility of peptides and proteins, are often added to sample solutions to improve the quality of spectra. The effect has been reported in the literature for the characterization of high molecular weight proteins in very dilute solutions. Use of detergents for cell profiling has extended the detectable mass range to about 75 kDa.

The surface tension of the solvent system must also be considered during the selection process. At low surface tension the matrix-analyte droplets spread over a large surface area resulting in a dilution effect and lowering the ion yields. In general, water-rich solvents exhibit adequate surface tension and allow the formation of reproducible round-shaped deposits with high crystal density. Low surface tension solvents, such as alcohols and acetone, provide wide spread and irregularly shaped crystal beds. Careful adjustment of the solvent surface tension is needed for MALDI targets with closely spaced sample wells and for sample preparation procedures relying on robotic sample loading.

The volatility of the solvent must also be considered. Fast solvent evaporation results in smaller crystals with more homogeneous analyte distributions. However, rapid crystallization also shows increased cationization, favors low molecular weight components in mixtures and provides very thin crystal beds that can only handle a few laser shots per spot. Volatile solvents require more skill from the operator since they must be handled quickly to avoid premature precipitation of the matrix in the pipette tips as caused by excessive solvent evaporation. Fast evaporating solvents such as acetone and methanol have reduced surface tension and form very wide and irregularly shaped MALDI deposits. The use of volatile solvents to obtain microcrystals during sample preparation can often be substituted with the "acetone redeposition" technique. In this technique, the dried MALDI sample (prepared with non-volatile solvents) is dissolved in a single drop of acetone and, as the acetone evaporates, the sample crystallizes to form a more homogeneous film.

Involatile solvents commonly used in protein chemistry must be avoided. Examples are glycerol, polyethyleneglycol, b-mercaptoethanol, dimethylsulfoxide, and dimethylformamide. These solvents interfere with matrix crystallization and coat any crystals that do form with a difficult to remove solvent layer. The crushed crystal method was specifically developed to deal with their presence.

The pH of the evaporating solvent system must be less than 4. Most of the MALDI matrix materials used for peptides and proteins are organic acids that become ions at pH>4, completely changing their crystallization properties. Solvent acidity affects the protein binding to matrix crystals and it can even modify the conformation of the proteins. Analyte conformation has been shown to influence MALDI Ion yields. The addition of trifluoroacetic acid (TFA) and formic acid (FA) to matrix solutions is common practice to assure the correct acidity during evaporation of the analyte-matrix droplet. Another common trick is to use 0.1% and 1% TFA, instead of pure water, as protein sample solvents. The acidity of the solution must be carefully optimized in MALDI of mixtures to assure no components are being excluded from the crystals.

The reactivity of the solvent system with the analyte must be contemplated. A common problem of using strongly acidic solvents is cleavage of acid-labile peptide bonds, such as aspartic acid's proline bond. Cleavage of this bond in small and large proteins has been observed after sample preparation and cleavage products increase in intensity with time.

A potential problem with using formic acid as a solvent, or solvent component, is its reactivity toward serine and threonine residues in proteins. Formyl esterification of those amino acids results in the production of satellite peaks at 28 Da intervals of higher molecular weight. As a result, exposure to formic acid should be avoided in any studies using exact mass measurements. If the procedure must use formic acid, exposure should be kept as short as possible. Formic acid, 70%, is the best solvent for CNBr peptide cleavage. Dilute HCl (0.1 N) may also be used; however, care must be taken to neutralize the solution's pH before evaporating the solvent to dryness. A protocol has been reported for deformylation of formylated peptides generated during CNBr cleavage by treatment with ethanolamine (Tan et al., 1983). Concentrated TFA is also known to react with free amino acids.

The composition of the solvent is an important parameter that can influence the outcome of a MALDI study. The selection of solvent components is affected by the analyte type and its molecular weight and by the matrix material being used. The solvent system must be capable of dissolving the matrix and the analyte at the same time. It must also allow for the selective inclusion of the analyte into the matrix crystals during the drying process.

Hydrophilic peptides and protein samples are usually dissolved in 0.1% TFA. Matrices are often dissolved, at higher concentrations, in solvent systems consisting of up to three components. Common matrix solvent components are acetonitrile (CH3CN), small alcohols (methanol, ethanol 2-propanol), formic acid, dilute TFA (0.1-1% v/v) and pure water. TFA seems to yield spectra with higher mass resolution than formic acid; however, and particularly for mixtures, it is always advisable to try a range of solvents.

Oligonucleotides are mostly dissolved in pure water. Although, it is advised in all cases to use HPLC-graded solvents, deionized $H_2O$ is recommended in the case of oligonucleotides. This is due to the fact that HPLC-grade water is acidic and can contain variable concentration of salts. The solvent most commonly used for HPA and THAP (oligonucleotide matrices) is a 1:1 v/v of $ACN/H_2O$. The additive that is used with these matrix solutions, ammonium bicitrate, is either dissolved in $H_2O$ and later mixed with the matrix solutions or the matrices are dissolved in a solution of ammonium bicitrate in $ACN/H_2O$.

In the analysis of organic molecules or polymers, it is important to first find the optimum solvent for the sample and from there, depending on what the appropriate matrix for that compound is, the matrix can be dissolved in the same solvent as the sample or in a solvent that is miscible with the analyte solution.

Hydrophobic peptides (not soluble in water) are dissolved in water-free systems such as chloroform/alcohol or formic acid/alcohol mixtures and the matrix is usually dissolved in the same or very similar solvent. A nonionic detergent is often added to improve solubility and ion yields.

Solvent proportions in a solvent mixture can affect the ion yields in a MALDI study. A complete sample preparation protocol should include optimization of the relative concentrations of solvents in a mixture. For example, it has been demonstrated that small variations in the water content of alcohol-water mixtures can significantly affect ion yields. Very often the choice of concentrations can be as critical as the choice of components.

The variety of choices and effects that MALDI users must consider during solvent optimization must not be considered as a drawback for the MALDI technique. It is in fact, the ability to operate with a wide range of solvents and in the presence of impurities that has allowed MALDI to be used for the mass spectrometric characterization of all kinds of biological and synthetic polymers.

D. Substrate Selection

When designing effective MALDI sample preparation methods for analysis, attention must be given to the interaction of analytes with the substrate.

Most MALDI samples are prepared on and desorbed/ionized from multi-well metallic sample-plates made out of vacuum compatible stainless steel or aluminum. The role of the metal substrate in the desorption/ionization process is not well understood, but the surface conductivity of the metal is often considered essential to preserve the integrity of the electrostatic field around the sample during ion ejection. The hard metals can be machined and formed to high precision, and can also be easily cleaned and polished to provide the smooth surfaces needed for high resolution and high mass accuracy. The analyte/matrix crystals strongly adhere to metal surfaces providing very rugged samples that can be stored for long periods of time and washed for purification purposes.

Both stainless steel and aluminum are chemically inert to the matrix systems used and do not contribute metal ions to the cationization of the analyte during ion formation. Copper as a substrate, on the other hand, has been demonstrated to form adducts with both matrix and analyte during desorption (Russell et al., 1999). The effect is particularly dramatic with the matrix CHCA and leads to several peaks at molecular weights above the protonated ions. The extra peaks are generally viewed as a problem for the analysis of proteins, particularly when they are not clearly resolved from the protonated ion signal. However, Cu adduction can be exploited in MALDI post-source decay studies because [M+Cu]+ ions fragment in ways different from the protonated ones, providing valuable extra sequencing information.

Most MALDI sources use a solid sample plate and irradiation is done from the front (reflection geometry); however, use of transmission geometry to desorb the analyte/matrix samples is possible. In the transmission geometry the laser irradiation and the mass spectrometer's analyzer are on opposite sides of the thin sample. The substrates used in the two case studies were quartz and plastic-coated grids (Formvar on zinc or copper).

Plastic is the second most common material used in MALDI sources as a substrate. Significant attention must be given to the interaction of the peptides and proteins with the polymeric surface (Kinsel et al., 1999). The influence of polymer surface-protein binding affinity on protein ion signals has been studied, and it showed that as the surface-protein binding affinity increases the efficiency of MALDI of the protein decreases.

Desorption of high mass proteins (>100 kDa), directly deposited on polyethylene membranes was demonstrated (Blackledge et al., 1995) and the spectra obtained were identical or better than with standard metal substrates. Similar improvements were observed by Guo (1999) while desorbing DNA and proteins directly from Teflon-coated MALDI probes. The use of a Nafion substrate with certain matrices can significantly enhance the signals obtained over those observed with a stainless-steel probe. Its use has been demonstrated to be particularly effective in analyzing real biological mixtures without pre-purification and used with polypropylene, polystyrene, teflon, nylon, glass and ceramics as matrix crystal supports with no noticeable decrease in performance relative to all-metal constructions (Hutchens et al., 1993).

The use of plastic membranes as sample supports has recently been adopted as a means of both sample purification and sample delivery into the mass spectrometer. If the analyte can be selectively adsorbed (hydrophobic interactions) onto the membrane, interfering substances can be washed off while the analyte is retained. Purification by on-probe washing results in lower sample loss than pre-purification by traditional methods. Polyethylene and polypropylene surfaces have been used to conduct on-probe sample purification. (Woods et al., 1998) Similarly, poly(vinylidene fluoride) based membranes have been used to extract and purify proteins from bulk cell extracts and for the removal of detergents, and a method has been developed for probe surface derivatization to construct monolayers of C18 on MALDI Probes (Orlando et al., 1997). Non-porous polyurethane membrane has been used as the collection device and transportation medium of blood sample analysis, followed by direct desorption from the same membrane substrate in a MALDI-TOF spectrometer (Perreault et al., 1998). Sample purification and proteolytic digest right on the probe tip, with minimal sample loss, was also possible with this substrate. Nitrocellulose, used as a sample additive or as a pre-deposited substrate, has been used by several researchers to improve MALDI spectra quality, to induce matrix signal suppression, and to rapidly detect and identify large proteins from *Escherichia coli* whole cell lysates in the mass range from 25-500 kDa.

Direct analysis of SDS-PAGE-separated proteins electroblotted onto membranes using MALDI-MS has been performed by a large number of MALDI users. In all cases, the membrane with the blotted protein spot is attached to the probe tip for direct MALDI analysis. The matrix is added to the protein spots by soaking the membrane with matrix solution. The incorporation of the proteins and peptides into the matrix crystals relies on the ability of the matrix solution to solvate the proteins adsorbed on the membrane. UV as well as IR irradiation are used to desorb/ionize the analyte molecules, with IR offering the advantage of larger penetration-depth into the membrane. Peptides produced after enzymatic or chemical digestion of proteins blotted onto a membrane have also been analyzed by MALDI, providing one of the fastest paths for protein identification after 2-D Gel separation. Poly(vinylidenefluoride) (PVDF) based membranes have been most commonly evaluated and used for these purposes. Other membranes, such as Nylon, Zitex, and polyethylene have also been found to be useful for the detection of dot blotted proteins by MALDI MS. A study demonstrates the capabilities of IR-MALDI can analyze electroblotted proteins directly from PVDF membranes, compare different membrane materials, and looks into on-membrane digestions and peptide mapping (Schleuder et al., 1999). The link between gel electrophoresis and MALDI MS has been taken one step further by introducing dried matrix-soaked gels into their mass spectrometers for direct MALDI analysis of the intact, and in-gel-digested, proteins (Philip et al., 1997). The method provides masses of both intact and cleavage products without the time and sample losses associated to electroelution or electroblotting. The key to their success is the use of ultrathin polyacrylamide gels, which dry to a thickness of 10 mm or less and which have the additional advantages of rapid preparation and electrophoresis run times. The methods are applied to isoelectric focusing (IEF), native and SDS-PAGE gels. When used in combination with IEF gels, this option makes it possible to run "virtual 2-D gels" in which proteins are resolved in the first dimension on the basis of their charge, whereas the second dimension is MALDI-MS-measured molecular weight instead of SDS-PAGE. The effects of the substrate on the MALDI signal must be carefully considered and accounted for in these studies. Mass accuracy in desorption from gels is an important concern. Several effects conspire against high mass accuracy determinations: (a) uneven gel thicknesses, (b) difficulty mounting gels flat and (c) surface charging of the dielectric material are the three most serious problems. Delayed extraction overcomes some of the mass accuracy limitations, and accuracy to better than 0.1% is readily obtained.

Another recent development in the MALDI field is the use of molecularly tailored MALDI-probe-substrates chemically modified to selectively capture specific analytes from solution prior to mass spectrometry (Hutchens et al., 1993). The efficacy of affinity capture techniques has been demonstrated (originally termed surface enhanced affinity capture (SEAC) mass spectrometry). In the published example of SEAC, agarose beads with attached single strand DNA were used to capture lactoferrin from pre-term infanturine. After these beads were incubated in the urine sample, the beads were removed, washed, placed directly on the MALDI probe tip and analyzed with conventional MALDI. The capture agent used as a substrate did not seem to degrade the performance of the MALDI-MS. Since this original report, on-probe immunoaffinity extraction has become common place in many laboratories, and there is even commercial sources that can supply affinity-capture probes tailored to specific analysis requirements.

Rapid peptide mapping has been accomplished using an approach in which the analyte is applied directly to a mass spectrometric probe tip that actively performs the enzymatic degradation, i.e., the probe substrate carries the enzymatic reagent. Applying the analyte directly to the probe tip increases the overall sensitivity of peptide mapping analysis. High on-probe enzyme concentrations provide digestion times in the order of a few minutes, without the adverse effect of autolysis peaks. Bioreactive probe tips have been used routinely for the proteolytic mapping and partial sequence determination of picomole quantities of peptide.

E. Crystallization Methods

With minor modifications, the original and simple sample preparation procedure introduced by Karas and Hillenkamp (1988) has remained intact for over a decade, and it is commonly referred to as the dried-droplet method: An aqueous solution of the matrix compound is mixed with analyte solution. A 1 mL droplet of this solution is then dried resulting in a solid deposit of analyte-doped matrix crystal that is introduced into the mass spectrometer for analysis.

The trick is to find matrix molecules that will dry out of solution with analyte molecules in the resulting matrix crystals and that will enable the MALDI process. Poor sample preparation will yield low resolution, poor reproducibility and degraded sensitivity. MALDI optimization is primarily an empirical process that involves a significant amount of trial-and-error. Every choice during sample preparation can potentially affect the outcome of the MALDI measurement. It is not unusual to test a few different approaches before choosing the optimum protocol for sample preparation. The following are a variety of methods used for crystallization.

1. Dried Droplet

The dried-droplet method is the oldest and has remained the preferred sample preparation method in the MALDI community.

Step-by-step procedure:
1. Prepare a fresh saturated solution of matrix material in the solvent system of choice: A small amount, 10-20 mg, of matrix powder is thoroughly mixed with 1 mL of solvent in a 1.5 mL Eppendorf tube, and then centrifuged to pellet the undissolved matrix.
2. Place 5-10 mL of the supernatant matrix solution in a small Eppendorf tube. (Note: Typical concentrations in saturated matrix-only solutions are in the 1-100 mM range.)
3. Add a smaller volume (1 to 2 mL) of protein solution (1-100 mM) to the matrix.
4. Mix the solution thoroughly for a few seconds in a vortex mixer.
5. Place a 0.5-2 mL droplet of the resulting mixture on the mass spectrometer sample plate.
6. Dry the droplet at room temperature. (Note: Blowing room-temperature air over the droplet speeds drying.)
7. When the liquid has completely evaporated, the sample may be loaded into the mass spectrometer. Typical analyte amounts on MALDI crystalline deposits are in the 0.1-100 picomole range.

The analyte/matrix crystals may be washed to etch away the involatile components of the original solution that tend to accumulate on the surface layer of the crystals (segregation). The procedure most often recommended is to thoroughly dry the sample (dessicator or vacuum dry) followed by a brief immersion in cold water (10 to 30 seconds in 4° C. water). The excess water is removed immediately after, by flicking the sample stage or by suction with a pipette tip.

This method is surprisingly simple and provides good results for many different types of samples. Dried droplets are very stable and can be kept in vacuum or refrigerator for days before running a MALDI study.

The dried-droplet method tolerates the presence of salts and buffers very well, but this tolerance has its limits. Washing the sample as described above can help; however, if signal suppression is suspected, a different approach should be tried (see crushed-crystal).

The dried-droplet method is usually a good choice for samples containing more than one protein or peptide component. The thorough mixing of the matrix and analyte prior to crystallization usually assures the best possible reproducibility of results for mixtures.

A common problem in the dried droplet method is the aggregation of higher amounts of analyte/matrix crystals in a ring around the edge of the drop. Normally these crystals are inhomogeneous and irregularly distributed, which is the reason MALDI users often end up searching for "sweet spots" on their sample surfaces. As an example, it has been observed that peptides and proteins tend to associate with the big crystals of 2,5-dihydroxybenzoic acid that form at the periphery of air dried drops containing aqueous solvent, whereas the salts are predominantly found in the smaller crystals formed in the center of the sample spot at the end of crystallization. In a clever set of studies, Li et al. (1996) used confocal fluorescence to demonstrate that with the dried-droplet method, the analyte is not uniformly distributed among or within the matrix crystals. In fact, some crystals show no analyte at all.

Most well-written MALDI software packages allow for automated sweet-spot searching during data acquisition, a procedure by which the sample surface is scanned with the laser beam until a portion yielding strong signals is located.

Another problem that is often observed during crystallization is what is known as segregation: as the solvent evaporates and the matrix crystallizes, the salts and some of the analyte are excluded from matrix crystals. This is particularly important in cases where cationization is the ionization mechanism, such as in the case of synthetic polymers and carbohydrates. Component segregation yields an inhomogeneous mixture of analyte throughout the sample, resulting in highly variable analyte ion production as the laser is moved across the sample surface.

2. Vacuum Drying

The vacuum-drying crystallization method is a variation of the dried-droplet method in which the final analyte/matrix drop applied to the sample stage is rapidly dried in a vacuum chamber. Vacuum-drying is one of the simplest options available to reduce the size of the analyte/matrix crystals and increase crystal homogeneity by reducing the segregation effect. It is not a widespread sample preparation method, because of its mixed results and extra hardware requirements.

Step-by-step procedure:
1. Prepare the analyte/matrix sample solution following steps 1 through 4 of the dried-droplet method.
2. Apply a 0.5 to 2 mL drop of the solution to the sample stage.
3. Immediately introduce the sample stage into a vacuum-sealed container and pump the sample down to <10−2 Torr with a vacuum pump. Wait until the solvent is completely evaporated.
4. Introduce the sample into the mass spectrometer.

The vacuum drying method offers the fastest way to dry a MALDI sample. Vacuum drying is 20 to 30 times faster than either air or heat drying. This is a very attractive feature for users running lots of samples, requiring high sample throughput, or dealing with low volatility solvents.

When it works, vacuum-drying provides uniform crystalline deposits with small crystals. It greatly improves spot-to-spot reproducibility and minimizes the need to search for "sweet spots." The formation of smaller crystals offers the added advantage of thinner samples and improved mass accuracy and resolution. Reductions in the amount of laser power required for ion formation have been reported for vacuum dried samples compared to similarly prepared air or heat dried samples.

The main disadvantages of vacuum-drying are that it is not guaranteed to work better than dried droplet in all cases, and it requires accessory vacuum hardware that many analytical laboratories might not have available. Peptides and proteins analyzed with the vacuum-drying method tend to exhibit extensive alkali cation adduction. This can be substantially reduced by washing the crystals directly on the probe with cold water. With evaporation times beyond 20 seconds in a vacuum system, the vacuum drying effects becomes less pronounced.

3. Crushed Crystal

The crushed-crystal method was specifically developed to allow for the growth of analyte doped matrix crystals in the presence of high concentrations of involatile solvents (i.e., glycerol, 6M urea, DMSO, etc.) without any purification.

Step-by-step procedure:
1. A fresh saturated solution of matrix material in the solvent system of choice is prepared in the same fashion as in step 1 of the dried-droplet method. The supernatant liquid is transferred to a separate container before use to eliminate the potential presence of undissolved matrix crystals.
2. An aliquot (5 to 10 mL) of the saturated matrix solution is mixed with the protein containing solution (1 to 2 mL) to produce a final protein concentration of 0.1-10 mM. This analyte/matrix solution is equivalent to the one that would be made in the simpler dried-droplet study. Note: Particular attention must be paid to eliminate the presence of particulate matter in this solution. Centrifuge, and use the supernatant, if necessary.

3. A 1 mL drop of the matrix-only solution is placed on the sample stage and dried in air. The deposit formed looks identical to what is typically obtained from a dried-droplet deposit.
4. A clean glass slide (or the flat end of a glass rod) is placed on the deposit and pressed down on to the surface with an elastic rod such as a pencil eraser. The glass surface is turned laterally several times to smear the deposit into the surface.
5. The crushed matrix is then brushed with a tissue to remove any excess particles (no need to be particularly gentle)
6. A 1 mL droplet of the analyte/matrix solution is then applied to the spot bearing the smeared matrix material.
7. Within a few seconds an opaque film forms over the substrate surface covering the metal.
8. After about 1 minute the sample is immersed in room temperature water to remove involatile solvents and other contaminants. Note that it is not necessary to let the droplet dry before washing: the film does not wash off easily.
9. The film is blotted with a tissue to remove excess water and allowed to dry before loading into the mass spectrometer.

The dried-droplet method is widely used because it is simple and effective. Good signals are obtained from initial solutions that contain relatively high concentrations of contaminants (salts and buffers). Many real analytical samples contain those materials and the capacity to tolerate these impurities has an enormous practical importance. However, there are limits to the contamination tolerance of the dried-droplet method. Particularly, the presence of significant concentrations of involatile solvents reduces, or totally eliminates, the ion signals. Examples of the most common of these solvents are dimethyl sulfoxide, glycerol and urea. Removal of the involatile solvents may not be possible if they are needed to dissolve or stabilize the analyte.

The dried-droplet method forms crystals randomly throughout the droplet as the solvent evaporates. The surface of the droplet is the preferred site for initial crystal formation. The crystals form at the liquid/air interface and are then carried into the bulk of the solution by convection. The final sample deposit is littered with those crystals, and if no involatile solvent is present they become adhered to the substrate. If involatile solvents are present, the crystals might either not form or remain coated with the solvent, preventing them from attaching to the substrate. Even if crystals are formed and the deposit is introduced into the mass spectrometer, a coating of involatile solvent usually suppresses the ion signals. Attempts to wash the crystals usually results in their loss, because they are not securely bonded to the substrate.

The crushed-crystal method is operationally similar to the dried-droplet method, but the results are very different, particularly in the presence of involatile solvents. In this method rapid crystallization directly on the metal surface is seeded by the nucleation sites provided by the smeared matrix bed that is crushed on the metal plate prior to sample application. Crystal nucleation shifts from the air/liquid interface to the surface of the substrate and microcrystals formed inside the solution where the concentrations change slower. The polycrystalline film adheres to the surface so the crystallization can be halted any time by washing off the droplet before its volume decreases significantly.

The films produced are also more uniform than dried-droplet deposits, with respect to ion production and spot-to-spot reproducibility.

The disadvantage of the crushed-crystal method is the increase in sample preparation time caused by the additional steps. It does not lend itself to automation for high throughput applications. It requires strict particulate control during solution preparation to eliminate the presence of undissolved matrix crystals that can shift the nucleation from the metal surface to the bulk of the droplet.

4. Fast Evaporation

The fast-evaporation method was introduced by Vorm et al. (1994) with the main goal of improving the resolution and mass accuracy of MALDI measurements. It is a simple sample preparation procedure in which matrix and sample handling are completely decoupled.

Step-by-step procedure:
1. Prepare a matrix-only solution by dissolving the matrix material of choice in acetone containing 1-2% pure water or 0.1% aqueous TFA. The concentration of matrix can range between the point of saturation or one third of that concentration.
2. Apply a 0.5 mL drop of the matrix-only solution to the sample stage. The liquid spreads quickly and the solvent evaporates almost instantaneously.
3. Check the resulting matrix surface for homogeneity. Apart from a slight thickening at the edges, no inhomogeneity should be visible by light microscopy (>10× magnification.
4. Apply a drop (1 mL) of sample solution (0.1-10 mM) on top of the matrix bed and allow to dry either by itself or in a flow of nitrogen.
5. After the drop has dried it is introduced into the mass spectrometer for analysis.

For crystal washing it is recommend to wash the crystals prior to their introduction into the TOF spectrometer. A large droplet of 5-10 mL of water or dilute aqueous organic acid (i.e., 0.1% TFA) is applied on top of the sample spot. The liquid is left on the sample for 2-10 seconds and is then shaken off or blown off with pressurized air. The procedure can be repeated once or twice. The washing liquid must be free of alkali metals and should be neutral or acidic (i.e., 0.1% TFA).

Pneumatic spraying: Pneumatic spraying of the matrix-only layer has been suggested as an alternative for fast evaporation. The process delivers stable and long lived matrix films that can be used to precoat MALDI targets.

The fast-evaporation method provides polycrystalline surfaces with roughnesses 10-100 times smaller than equivalent dried-droplet deposits. Confocal fluorescence studies demonstrated that, across an entire sample deposition area, the analyte is more uniformly distributed than with the dried-droplet method.

The improved homogeneity of the sample surface provides several advantages. (1) Faster data acquisition. All spots on the surface result in similar spectra under the same laser irradiance. No sweet-spot hunting and less averaging. The outcome of the first few laser shots is usually enough to decide the outcome of a study. (2) Better correlation between signal and analyte concentration (still not a quantitative technique). (3) More reproducible sample-to-sample results. (4) Improved sensitivity. The peptides have been detected down to the attomole level. The higher ion signals are explained as the result of the increased surface area of the smaller crystals combined with the preferential localization of the analyte molecules on the outer layers of the crystals from where the MALDI signal is believed to originate. (5) Improved washability. Salts and impurities are more easily washed off the sample deposits because the crystals are more securely bonded to the metal surface and to each other. (6) Improved resolution and mass measurement accuracy. Resolution improvements of at least a factor of two have been reported compared to dried-droplet results. The improved mass accuracy can often eliminate the need for internal standards. (7) Matrix surfaces can be prepared in advance. Precoated sample plates prepared by fast-evaporation of matrix solution on the sample spots are available from a few commercial sources.

Some of the disadvantages that have been associated with this method are as follows. (1) It does not provide reproducible sample-to-sample data for peptide and protein mixtures. If the protein or peptide sample contains more than one component, it is best to try the dried-droplet or overlayer method first. The thorough mixing of the analyte and matrix solutions prior to deposition increases the reproducibility of the spectra obtained. (2) Because the layer of protein-doped matrix on each crystal is usually very thin, it only produces ions for a few shots on a laser spot. The laser spot must constantly move to a fresh location to maintain the signal levels. This results in reduced duty cycle for the data acquisition loop, and reduced throughput. (3) Working with very volatile solvents such as acetone makes it difficult to make reproducible sample spots. The solvent has a small surface tension and it spreads uncontrollably along the metal surface. Some varying amount of solvent is always lost to evaporation before the matrix-only droplet is delivered. (4) The method is very effective for the analysis of peptides but is not as effective for proteins. The two-layer method should be tried first in the case of proteins.

5. Overlayer (Two-Layer, Seed Layer)

The overlayer method was developed on the basis of the crushed-crystal method and the fast-evaporation method. It involves the use of fast solvent evaporation to form the first layer of small crystals, followed by deposition of a mixture of matrix and analyte solution on top of the crystal layer (as in the sample matrix deposition step of the crushed-crystal method). The origin of this method, and its multiple names, can be traced back to the efforts of several research groups (Li et al., 1999).

Step-by-step procedure:

1. First-layer solution (matrix only): Prepare a concentrated (5-50 mg/mL) matrix-only solution in a fast evaporating solvent such as acetone, methanol, or a combination of both.
2. Second-layer solution (analyte/matrix): Prepare the second-layer solution following the three steps below: Prepare a fresh saturated solution of matrix material in the solvent system of choice: A small amount, 10-20 mg, of matrix powder is thoroughly mixed with 1 ml of solvent in a 1.5 ml Eppendorf tube, and then centrifuged to pellet the undissolved matrix. Place 5-10 mL of the supernatant matrix solution in a small Eppendorf tube. Add a smaller volume (1 to 2 mL) of protein solution (1-100 mM) to the matrix. Mix the solution thoroughly for a few seconds in a vortex mixer. This is the second-layer solution.
3. Apply a 0.5 mL drop of the first-layer solution to the sample plate and let it dry to form a microcrystalline layer.
4. Apply a 0.5-1 mL drop of the second-layer solution on top of the crystal bed and allow to air dry. Note: If the first crystal layer is completely dissolved, stop and retry using a smaller volume of second-layer solution or a different solvent system.

Washing the crystals prior to introduction into the TOF spectrometer is often recommended. A large droplet of 5-10 mL of water or dilute aqueous organic acid (0.1% TFA) is applied on top of the sample spot. The liquid is left on the sample for 2-10 seconds and is then shaken off or blown off with pressurized air. The procedure can be repeated once or twice. The washing liquid must be free of alkali metals and should be neutral or acidic (i.e., 0.1% TFA).

The difference between the fast evaporation and the overlayer method is in the second-layer solution. The addition of matrix to the second step is believed to provide improved results, particularly for proteins and mixtures of peptides and proteins.

The overlayer method has several convenient features that make it a very popular approach. (1) It naturally inherits all the advantages detailed in the fast evaporation method, and it avoids some of its limitations. (2) It provides enhanced sensitivity and excellent spot-to-spot reproducibility for proteins beyond what is possible with the fast-evaporation method. This enhancement is likely due to improved matrix isolation of the analyte molecules on the crystal surfaces in the presence of the surplus of matrix molecules. (3) With the careful optimization of the second-layer analyte/matrix solution, the overlayer method is found to be very effective for the analysis of complicated mixtures containing both peptides and proteins. The ability to manipulate the second layer conditions adds flexibility to the sample preparation.

6. Sandwich

The sandwich method is derived from the fast-evaporation method and the overlayer method. It was reported for the first time by Li (1996), and used for the analysis of single mammalian cell lysates by mass spectrometry. The report also included the description of a Microspot MALDI sample preparation to reduce the sample presentation surface to a minimum.

In the sandwich method the sample analyte is not premixed with matrix. A sample droplet is applied on top of a fast-evaporated matrix-only bed as in the fast-evaporation method, followed by the deposition of a second layer of matrix in a traditional (non-volatile) solvent. The sample is basically sandwiched between the two matrix layers.

7. Spin Coating

The preparation of near homogeneous samples of large biomolecules, based on the method of spin-coating sample substrates was reported for the first time by Perera (1995). In the original report, samples were deposited on 1" diameter stainless steel and quartz plates, and large volumes (3-10 mL) of the premixed sample solution were used. The spin coater was home-built and it operated at about 300 rpm, producing evenly spread crystal deposits in air. The samples were very homogeneous and generated highly reproducible and much enhanced molecular-ion yields from all regions of the sample target.

Spin coating the analyte/matrix samples works well and it usually delivers more homogeneous deposits on single-spot sample stages. However, it is not a viable option for MALDI plates with multiple sample wells of the kind found in all modern commercial instruments.

8. Slow Coating

It is possible to grow large, protein doped matrix crystals under near equilibrium conditions, rather than in a rapidly drying droplet (Beavis and Xiang, 1993). Supersaturated matrix solutions containing protein will form crystals that can be used directly in an ion source. Supersaturation can be achieved by heating, cooling or slow evaporation. The protein-doped crystals can be cleaved to expose well defined faces to the laser beam.

In general the slow crystallization approach favors the detection of high mass components over low mass peptides, regardless of pH and solution.

Producing large protein-doped crystals has several disadvantages compared to the fast drying (non-equilibrium) crystallization techniques described elsewhere: (1) It is slower. Crystals take hours to grow, definitely not practical for large-scale, high-throughput applications. (2) Peak broadening is often observed. (3) High mass accuracy is out of the question due to the irregular geometry of the sample bed. (4) Growing crystals requires more analyte (10-100×) than traditional methods.

However, even with those difficulties some advantages are also realized: (1) Crystals can be grown from solutions with involatile solvents at concentrations that suppress ion signals from dried droplet studies. (2) High concentrations of non-protenaceous solutes do not affect crystal doping. Detergents are an exception. (3) Mixtures of polypeptides can be incorporated into crystals and analyzed. (4) Crystals can be easily manipulated. Common operations are washing, cleaving, etching and mounting. (5) The crystals are very rugged. (6) The crystals provide more defined starting conditions for fundamental MALDI ionization mechanism studies.

9. Electrospray

Electrospray as a sample deposition for MALDI-MS was suggested by Owens et al., 1997). In this technique, a small amount of matrix-analyte mixture is electrosprayed from a HV-biased (3-5 KV) stainless steel or glass capillary onto a grounded metal sample plate, mounted 0.5-3 cm away from the tip of the capillary.

Electrospray sample deposition creates a homogenous layer of equally sized microcrystals and the guest molecules are evenly distributed in the sample. The method has been proposed to achieve fast-evaporation and to effectively minimize sample segregation effects. The presence of cation adducts in the MALDI spectra from electrodeposited samples demonstrates that solution components are less segregated than in equivalent dried-droplet deposits.

Electrospray matrix deposition was used (Caprioli et al., 1997) to coat tissue samples during the MALDI based molecular imaging of peptides and proteins in biological samples. Matrix-only solution was electrosprayed on TLC plates for the direct MALDI analysis of the impurity spots of tetracycline samples (Clench et al., 1999).

Electrospray deposited samples have been shown to give several advantages over traditional droplet methods: (1) The reproducibility of MALDI results from spot-to-spot within one sample deposit, and from sample-to-sample for multiple depositions, is much improved. Typical sample-to-sample variations are in the 10 to 20% range. (2) The correlation between analyte concentration and matrix signal is also improved. Quantitation with internal standards has been reported by Owens. (3) The sample deposits are much more resistant to laser irradiation. More shots can be collected from any single laser spot location. (4) The method offers a possible path for interfacing MALDI sample preparation to Capillary electrophoresis and liquid chromatography.

Disadvantages: (1) Slower. It takes 1 to 5 minutes to create a useful deposit. It also takes time to switch to a new analyte since the capillary must be thoroughly cleared of any leftover sample from the last measurement before spraying can start. (2) Salt adducts are a problem and desalting of the matrix and the sample is usually needed to eliminate cationization signals. (3) Extra equipment is required, along with training. (4) It involves the use of dangerous high voltages.

Aerospray (pneumatic spraying) has been suggested as an alternative sample spraying method. Recent results have demonstrated high degree of reproducibility for this sample preparation technique (Wilkins et al., 1998). Homogeneous thin films can be easily made, with good spot-to-spot and sample-to-sample reproducibility.

The potential exists to combine both techniques, using aerospray for the nebulization and an electric field to control solvent evaporation and droplet size.

10. Matrix Pre-Coated Targets

The use of matrix-precoated targets for the MALDI analysis of peptides and proteins has been investigated by several research groups. It is easy to realize the advantages of a sample preparation method reduced to the straightforward addition of a single drop of undiluted sample to a precoated target spot. Such a method would not only be faster and more sensitive than the ones described before, but it would also offer the opportunity to directly interface the MALDI sample preparation to the output of LC and CE columns.

Early efforts described the use of a pneumatic sprayer to fast-evaporate a thin matrix-only layer on a MALDI target (Kochling and Biemann, 1995). The microcrystalline films were very stable and long-lived and provided adequate MALDI spectra for peptides and small proteins.

Most other efforts have focused on the development of thin-layer matrix-precoated membranes. Particular attention has been dedicated to the choice of membrane material. Some of the options that have been tested (with varying results) include: nylon, PVDF, nitrocellulose, anion- and cation-modified cellulose and regenerated cellulose. Particularly encouraging results, in terms of sensitivity and quality of spectra, were obtained by Zhang and Caprioli (1996) for regenerated cellulose dialysis membrane. Their membrane precoating procedure provided results comparable to dried-droplet method for peptides and small proteins under 25 KDa. Heavier proteins (>25 KDa) gave poorer results, presumably due to the limited amount of matrix available in the precoated membranes and/or the inability to form protein doped microcrystals.

It has been observed that using nitrocellulose in a sample preparation for MALDI-TOF MS of peptides can increase ion yields (Preston et al., 1993). Mass spectrometry and optical microscopy results suggest that the nitrocellulose addition modifies the crystallization of the matrix-analyte solution to allow more even coverage over the sample surface.

Hutchens (1993) developed a sample preparation technique they called Surface-Enhanced Neat Desorption (SEND) in which energy-absorbing-molecules were bound to substrates to provide chemically modified surfaces capable of desorbing "neat" analyte ions. The results were very encouraging, but the technique was never mainstreamed into the general MALDI methodology.

III. Methods

The present invention may be exploited in a variety of ways. In particular embodiments, one may obtain information regarding disease states such as hyperproliferative diseases (e.g., cancers), inflammatory diseases, infectious diseases, genetic or developmental diseases, or responses to environmental insults (e.g., poisons or toxins). By identifying the aberrant expression or localization of target molecules, one can gain an increased understanding of the disease state. This in turn will permit one to diagnose disease based on molecular rather than clinical symptoms, and to monitor disease states, particular during the course of therapy to determine response.

Moreover, the given the number of changes that can be observed, the ability to distinguish normal form abnormal tissue is greatly enhanced. This could be particularly important in providing early stage diagnosis of pathologic events, thereby permitting earlier therapeutic intervention. This technology also may be applied to assessing the efficacy of surgical removal of diseased tissue, or to identifying the margins of diseased tissue during surgery.

In another application, the present invention may be used to screen for therapeutic methods. In one scenario, one can assess a plurality of disease markers, including those that are both up- and down-regulated in the disease state, at the same time and in the same sample. Providing a drug to a cell, tissue or organism, followed by obtaining expression level or localization using the mass tag complexes of the present invention, permits one to assess the impact of the drug on multiple relevant disease markers.

In an additional embodiment, one may screen for the presence of drug metabolites or other metabolic compounds, including both their quantitation and localization. This may be done in conduction with, or separately from, assessment of nucleic acid and proteins that are impacted by the drug.

IV. Kits

The mass tag complexes, or components thereof, may be comprised in a kit. The kits will thus comprise, in suitable container means, a mass tag complex or population thereof, or the individual mass tags, cores, cleavage sites other reagents for the preparation of mass tag complexes.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed.

The kits of the present invention also will typically include a means for containing the reagent containers in close confinement for commercial sale. Such containers may include injection or blow-molded plastic containers into which the desired vials are retained.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effects of Tissue Fixation with Ethanol on Mass Spectrometry Analysis

An important component for the overall success of this proposal is the effectiveness of the tissue processing protocols prior to in situ hybridization and IMS analysis. To accurately reflect the biological conditions present in the tissues of interest, the tissue must be processed appropriately to maintain the integrity of the RNA without a loss to the overall structure of the tissue section, allowing effective detection of the mass probe tags during IMS. Others have published significantly on tissue processing for IMS in breast, colon and prostate tissue samples (Chaurand et al., 2001a; Chaurand et al., 2001b; Masumori et al., 2001; Xu et al., 2002). Additionally, a recent report from Kruse and Sweedler describes the evaluation and optimization of several tissue fixation and processing methods for invertebrate ganglia prior to IMS (Kruse and Sweedler, 2003).

Typical tissue fixative and processing methods used for traditional optical or electron microscopy are not compatible with MALDI-TOF MS. When used in MALDI procedures, these processing methods suffer from several problematic features such as chemical modification of peptides, suppression of peptide signal and disruption of morphological integrity (Kruse and Sweedler, 2003). Fixatives acting as cross linking reagents are not acceptable due to chemical interactions with analytes (Rubbi et al., 1994; Sung et al., 2001). Based on these results, fixative agents will be avoided whenever possible in the processing of tissue samples.

Based on procedures increasing and then decreasing concentrations of ethanol in phosphate buffer. FIG. 1 shows the results of a liver section processed with ethanol compared to untreated and water treated sections. Although there were concerns that the ethanol processing could remove soluble proteins, no significant protein loss was observed following the graded alcohol washes. Additionally, no structural changes were observed by light microscopy (data not shown).

Example 2

Detection of a 6-Residue Poly-Tyrosine Tag by IMS

The effective detection of the various mass tags during IMS analysis is important to the success of the studies presented herein. Although MALDI-TOF MS can detect very small amounts of material with mass ranges well below 200, the conditions encountered during IMS are significantly different than those optimized for analyte detection. Unlike studies performed with somewhat defined components on a mass spectrometry plate, the presence of the intact tissue section generally causes an increase in background in the lower mass regions during IMS. This background signal is from matrix crystals, peptide fragments and other ionizable low molecular weight species present in the tissue.

Figure 2:
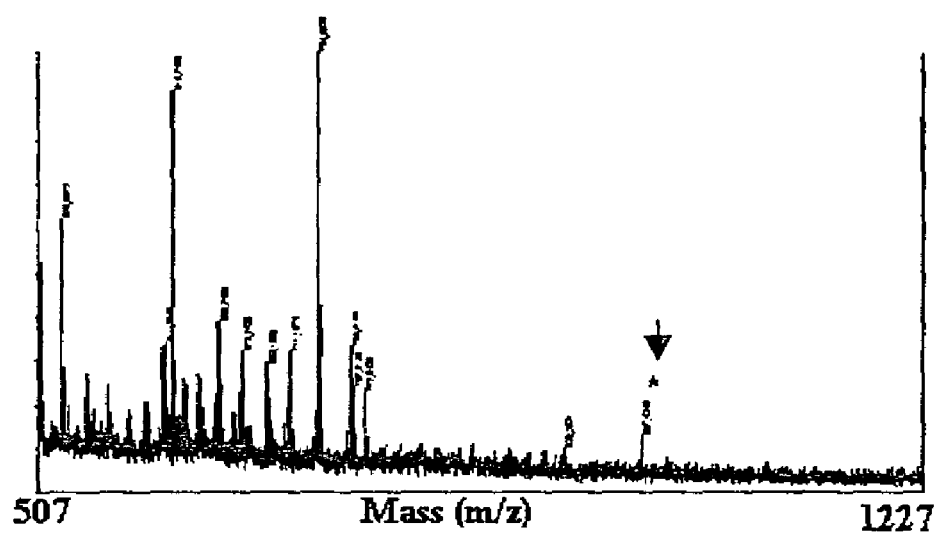
FIG. 2—IMS spectra showing detection of a 6-residue poly-tyrosine peptide spotted onto a 12 μm section of mouse brain. Mass peak indicated by arrow; * represents the peak for approximately 20 fmol of material. Mass range shown is 507 to 1227.
Figure 3:
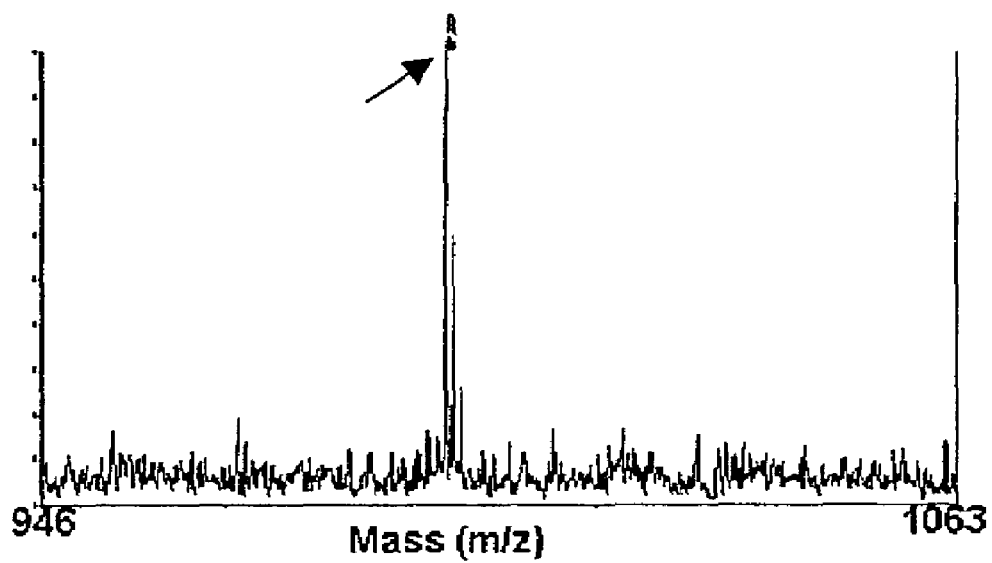
FIG. 3—IMS spectra showing the detection of a 6-residue poly-tyrosine peptide spotted onto a 12 μm section of mouse brain. The mass peak indicated by arrow and * represents the peak for approximately 20 fmol of material. Mass range shown in 946 to 1063.

The ability to successfully and specifically detect the peptide tags in a background of peptide signals from complex tissues signals is illustrated in FIGS. 2 and 3. A 12 µm section of mouse brain was coated with sinapinic acid (SA) and analyzed by IMS. To simulate the presence of a peptide tag, a range of concentrations of 6-residue polytyrosine was spotted onto the tissue section prior to analysis. The spectra shown in FIGS. 2 and 3 illustrate the lower end of the detection range for the peptide while still maintaining a signal-to-noise ratio of at least 5. The final amount of poly-tyrosine shown in FIGS. 2 and 3 was 400 pmol. Because the diameter of the laser was significantly smaller than the area covered by the 0.25 µl spot, approximately 2-5% of the spot area is ionized in each spectrum, giving a final detection threshold of approximately 12 fmol. This level of detection is similar to that observed for other quantitation standards used by our collaborators. FIG. 2 shows an increased mass range compared to FIG. 3, clearly showing that background signals begin to severely limit the detection of molecules at m/z values less than 800. The total mass of the smallest mass tag described in this proposal is just under 1000. Since the poly-tyrosine peptide used in FIGS. 2 and 3 did not have the photocleavable linker, the mass is almost identical to the polyserine mass tag. The background levels that are observed above m/z of 800 are acceptable and should provide reasonable detection range for a variety of mass tags with molecular weights above 900 and amounts to 15-20 fmol.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,196,265
U.S. Pat. No. 4,659,774
U.S. Pat. No. 4,682,195
U.S. Pat. No. 4,683,202
U.S. Pat. No. 4,816,571
U.S. Pat. No. 4,959,463
U.S. Pat. No. 5,141,813
U.S. Pat. No. 5,214,136
U.S. Pat. No. 5,223,618
U.S. Pat. No. 5,264,566
U.S. Pat. No. 5,378,825
U.S. Pat. No. 5,428,148
U.S. Pat. No. 5,446,137
U.S. Pat. No. 5,466,786
U.S. Pat. No. 5,470,967
U.S. Pat. No. 5,539,082
U.S. Pat. No. 5,554,744
U.S. Pat. No. 5,574,146
U.S. Pat. No. 5,602,240
U.S. Pat. No. 5,602,244
U.S. Pat. No. 5,610,289
U.S. Pat. No. 5,614,617
U.S. Pat. No. 5,623,070
U.S. Pat. No. 5,645,897
U.S. Pat. No. 5,652,099
U.S. Pat. No. 5,670,663
U.S. Pat. No. 5,672,697
U.S. Pat. No. 5,681,947
U.S. Pat. No. 5,700,922
U.S. Pat. No. 5,705,629
U.S. Pat. No. 5,714,331
U.S. Pat. No. 5,714,606
U.S. Pat. No. 5,719,262
U.S. Pat. No. 5,736,336
U.S. Pat. No. 5,763,167
U.S. Pat. No. 5,766,855
U.S. Pat. No. 5,766,855
U.S. Pat. No. 5,773,571
U.S. Pat. No. 5,777,092
U.S. Pat. No. 5,786,461
U.S. Pat. No. 5,786,461
U.S. Pat. No. 5,792,847
U.S. Pat. No. 5,858,988
U.S. Pat. No. 5,859,221
U.S. Pat. No. 5,872,232
U.S. Pat. No. 5,886,165
U.S. Pat. No. 5,891,625
U.S. Pat. No. 5,908,845
Bahr et al., *J. Mass Spectrom.*, 32:1111-1116, 1997.
Beavis and Xiang, *Org. Mass Spectrom.* 28:1424, 1993.
Bentzley et al., *Anal Chem.*, 68(13):2141-2146, 1996.
Blackledge et al., *Anal. Chem.*, 67:843, 1995
Brown et al., *Proc. of the 45th ASMS Conf. on Mass Spectrom. & Allied Tops.*, 1997.
Campbell et al., *Am. Rev. Respir. Dis.*, 130(3):417-423, 1984.
Caprioli et al., *Anal. Chem.*, 69:4751-4760, 1997.
Chaurand et al., *Anal Chem.*, 71(23):5263-5270, 1999.
Chaurand et al., *Biochemistry*, 40:9725-9733, 2001.
Chaurand et al., *Proteomics*, 1:1320-1326, 2001.
Clench et al., *Rapid Commun. Mass Spectrom.*, 13:264, 1999.
Desiderio et al., *J. Mass Spectrom.*, 35(6):725-733, 2000
Duncan et al., *Rapid Commun. Mass Spectrom.*, 7:1090, 1993.
EP 266 032
Faulstich et al., *Anal. Chem.*, 69(21):4349-4353, 1997
Froehler et al., *Nucleic Acids Res.*, 14(13):5399-5407, 1986.
Gefter et al., *Somatic Cell Genet.*, 3:231-236, 1977.
Gobom et al., *Anal. Chem.* 72:3320, 2000.
Goding, In: *Monoclonal Antibodies: Principles and Practice*, 2d ed., Academic Press, FL., 60-66, and 71-74, 1986.
Guo et al., *Bioorg. Med. Chem. Lett.*, 9:419, 1999.
Gygi et al., *Nat. Biotechnol.*, 17:994-999, 1999.
Han et al., *Nat. Biotechnol.*, 19:946-951, 2001.
Harlow and Lane, In: *Antibodies: A Laboratory Manual*, Cold Spring Harbor Laboratory, Cold Spring Harbor, N.Y., 346-348, 1988.
Horak et al., *Rapid Commun. Mass Spectrom.*, 15(4):241-248, 2001
Hutchens et al., *Rapid Commun. Mass Spectrom.*, 7:5776, 1993.
Jespersen et al., *Anal Chem.*, 71(3):660-666, 1999.
Jiang et al., *J. Agric. Food Chem.*, 48:3305, 2000.
Kanazawa et al., *Biol. Pharm. Bull.*, 22(4):339-346, 1999.
Karas and Hillenkamp, *Anal. Chem.*, 60:2299-2301, 1988.
Kazmaier et al., *Anesthesiology*, 89(4):831-817, 1998.
Kinsel et al., *Anal. Chem.*, 71:268, 1999.
Kochling and Biemann, *Proc. of the 43rd Annual ASMS Conf. on Mass Spectrom. and Allied Topics*, 1995.
Kohler and Milstein, *Eur. J. Immunol.*, 6:511-519, 1976.
Kohler and Milstein, *Nature*, 256:495-497, 1975.
Koomen et al., *J. Mass Spectrom.*, 35:258-264, 2000.
Kornberg and Baker, *DNA Replication*, 2nd Ed., Freeman, San Francisco, 1992.
Kruse and Sweedler, *J. Am. Soc. Mass Spectrom.*, 14:752-759, 2003.
Li et al., *Anal. Chem.*, 71:5451, 1999.
Li et al., *J. Am. Chem. Soc.*, 118:11662, 1996.
Li et al., *Trends Biotechnol.*, 18:151, 2000.
Marie et al., *Anal. Chem.*, 72(20):5106-5114, 2000
Masumori et al., *Cancer Res*, 61:2239-2249, 2001.
Miketova et al., *Mol. Biotechnol.*, 8(3):249-253, 1997

Mirgorodskaya et al., *Rapid Commun. Mass Spectrom.,* 14:1226, 2000.
Muddiman et al., *Fres. J. Anal. Chem.,* 354:103, 1996.
Muller et al., *Acta,* 84:3735-3741, 2001.
Muller et al., *Helv. Chim. Acta,* 84:3735-7341, 2001.
Nelson et al., *Anal. Chem.,* 66:1408, 1994.
Nguyen et al., *J. Chromatogr. A.,* 705(1):21-45, 1995.
Olejnik et al., *Nucleic Acids Research,* 27, 4626-4631, 1999.
Onnerfjord et al., *Rapid Commun. Mass Spectrom.,* 13:315-322, 1999.
Orlando et al., *Anal. Chem.,* 69:4716, 1997.
Owens et al., *Rapid Commun. Mass Spectrom.,* 11:209, 1997.
PCT Appln. EP/01219
PCT Appln. WO 92/20702
Perera et al., *Rapid Commun. Mass Spectrom.,* 9:180, 1995.
Perreault et al., *Anal. Chem.,* 70:5142, 1998.
Philip et al., *Electrophoresis,* 18:382, 1997.
Preston et al., *Biol. Mass Spectrom.,* 22(9):544-550, 1993.
Roepstorff, *EXS.,* 88:81-97, 2000.
Rubakhin, et al., *J. Neurophysiol.,* 81:1251-1260, 1999.
Rubbi et al., *Eur. J. Histochem.,* 38:269-280, 1994.
Russell et al., *Int. J. Mass Spectrom.,* 182/183, 1999.
Sambrook et al., In: *Molecular cloning,* Cold Spring Harbor Laboratory Press, Cold Spring Harbor, N.Y., 2001.
Scheit, In: *Synthesis and Biological Function,* Wiley-Interscience, NY, 171-172, 1980.
Schleuder et al., *Anal. Chem.,* 71:3238, 1999.
Spengler and Hubert, *J. Am. Soc. Mass Spectrom.,* 13:735-748, 2002.
Stetsenko et al., *J. Org. Chem.,* 65, 4900-4908, 2000.
Stoeckli et al., *Nat. Med.,* 7:493-496, 2001.
Sung et al., *J. Biomed. Mater Res.,* 55:538-546, 2001.
Takach et al., *J. Protein Chem.,* 16:363, 1997.
Tan et al., *Anal. Biochem.* 131:99, 1983.
Todd et al., *J. Mass Spectrom.,* 36:355-369, 2001.
Villanueva et al., *Enzyme Microb. Technol.,* 29:99, 1999.
Vorm et. al., *Anal. Chem.,* 66:3281, 1994.
Wang et al., *Anal. Chem.,* 72(21):5285-5289, 2000.
Wang et al., *J. Exp. Med.,* 190:983, 1999.
Wilkins et al., *J. Am. Soc. Mass Spectrom.* 9:805, 1998.
Wittmann et al., *Biotechnol. Bioeng.,* 72:642, 2001.
Woods et al., *Anal. Chem.,* 70:750, 1998.
Wu et al., *Anal. Chem.,* 70:456A, 1998.
Wu et al., *Biochem. Biophys. Res. Commun.,* 233(1):221-6, 1997.
Xu et al., *J. Am. Soc. Mass Spectrom.,* 13:1292-1297, 2002.
Yang et al., *J. Biol. Chem.,* 275:26892-36898, 2000.
Zhang and Caprioli, *J. Mass Spectrom.,* 31:690, 1996.
Zhou et al., *Nat. Biotechnol.,* 20:512-515, 2002.
Zaluzec et al., *Protein Expr. Purif.,* 6:109-123, 1995.

The invention claimed is:

1. A mass tag complex comprising:
   (i) a water-soluble core structure;
   (ii) a target binding agent;
   (iii) a mass unit that permits detection by mass spectroscopy; and
   (iv) a cleavage site connected to said mass unit.

2. The complex of claim 1, further comprising a spacer unit connected to said cleavage site and/or said target binding agent.

3. The complex of claim 1, wherein said cleavage site is susceptible to photocleavage, chemical cleavage or enzymatic cleavage.

4. The complex of claim 1, wherein said mass unit is a peptide.

5. The complex of claim 1, wherein said target binding agent is an oligonucleotide that hybridizes to an RNA of interest.

6. The complex of claim 5, wherein said oligonucleotide is about 8 to about 25 bases in length.

7. The complex of claim 1, wherein said target binding agent is an antibody that binds to a protein of interest.

8. The complex of claim 7, wherein said antibody is Ig, F(ab), F(ab')$_2$ or single chain.

9. The complex of claim 1, wherein said core structure is a polar-neutral, water-soluble structure.

10. The complex of claim 1, wherein each of said target binding agent and said mass unit is independently linked to said core structure.

11. A population of mass tag complexes, each complex comprising:
    (i) an identical core structure;
    (ii) a target binding agent, wherein said population comprises a plurality of target binding agents with different target binding specificities;
    (iii) a mass unit that permits detection by mass spectroscopy, wherein said population comprises a plurality of mass units that have different masses that can be differentiated by said mass spectroscopy; and
    (iv) a cleavage site connected to said mass unit.

12. The population of claim 11, wherein each complex further comprises a spacer unit connected to said each of cleavage sites and/or said target binding agents.

13. The population of claim 11, wherein each of said mass units is a peptide.

14. The population of claim 11, wherein each of said cleavage sites is photocleaved, enzymatically cleaved or chemically cleaved.

15. The population of claim 11, wherein said each of said target binding agents is an oligonucleotide that hybridizes to a different RNA of interest.

16. The population of claim 15, wherein each of said oligonucleotides is about 8 to about 25 bases in length.

17. The population of claim 11, wherein each of said target binding agents is an antibody that binds to a different protein of interest.

18. The population of claim 17, wherein each of said antibodies is Ig, F(ab), F(ab')$_2$ or single chain.

19. The population of claim 11, wherein each of said core structures is a polar-neutral, water-soluble structure.

20. The population of claim 11, wherein each of said target binding agents and said mass units is independently linked to said core structure.

21. A method of simultaneously obtaining information on a plurality of distinct biomolecules comprising:
    (a) providing a population of mass tag complexes, each complex comprising:
        (i) an identical core structure;
        (ii) a target binding agent, wherein said population comprises a plurality of binding agents with different target binding specificities;
        (iii) a mass unit that permits detection by mass spectroscopy, wherein said population comprises a plurality of mass units that have different masses that can be differentiated by said mass spectroscopy; and
        (iv) a cleavage site connected to said mass unit;
    (b) contacting said population with a biomolecule-containing sample;
    (c) cleaving said cleavage site; and
    (d) subjecting said sample to mass spectroscopy.

22. The method of claim 21, wherein said mass spectroscopy is MALDI-TOF.

23. The method of claim 21, wherein cleavage site is photocleaved, and step (c) comprises subjecting said sample to an appropriate light source.

24. The method of claim 21, further comprising the step, between steps (b) and (c), of spatially fixing said biomolecules and target binding agents.

25. The method of claim 24, wherein said biomolecules and target binding agents are located in a cell.

26. The method of claim 25, wherein said cell is from a patient with a pathologic condition.

27. The method of claim 26, wherein said pathologic condition is cancer, an inflammatory disease, an infection, or a developmental disease.

28. The method of claim 25, wherein said cell or patient has been treated with a therapy.

29. The method of claim 25, wherein said cell is in comprised within an intact tissue specimen or an organism.

30. The method of claim 21, wherein said mass unit is a peptide.

31. The method of claim 21, wherein each of said target binding agents is an oligonucleotide that hybridizes to a different RNA of interest.

32. The method of claim 31, wherein said oligonucleotide is about 8 to about 25 bases in length.

33. The method of claim 21, wherein each of said target binding agents is an antibody that binds to a different protein of interest.

34. The method of claim 33, wherein said antibody is Ig, F(ab), F(ab')$_2$ or single chain.

35. The method of claim 21, wherein said core structure is a polar-neutral, water-soluble structure.

36. A method of obtaining information on the spatial position of a biomolecule in a cell comprising:
    (a) providing a mass tag complex comprising:
        (i) a core structure;
        (ii) a target binding agent;
        (iii) a mass unit that permits detection by mass spectroscopy, wherein said population comprises a plurality of mass units that have different masses that can be differentiated by said mass spectroscopy; and
        (iv) a cleavage site connected to said mass unit;
    (b) contacting said mass tag complex with a cell-containing sample;
    (c) spatially fixing said biomolecule and target binding agent;
    (d) cleaving said cleavage site; and
    (e) subjecting said sample to mass spectroscopy.

37. The method of claim 36, further comprising obtaining information on the expression level of said biomolecule.

38. The method of claim 36, further comprising obtaining information on a plurality of biomolecules by providing a population of mass tag complexes, each complex comprising an identical core structure; a target binding agent with a distinct target specificity; a distinct mass unit that permits detection by mass spectroscopy; and a cleavage site connected to said mass unit.

39. The method of claim 38, wherein said biomolecule is an RNA or a protein.

40. The method of claim 36, wherein said cell is located in an intact tissue specimen or an organism.

* * * * *

UNITED STATES PATENT AND TRADEMARK OFFICE
CERTIFICATE OF CORRECTION

PATENT NO.         : 7,569,392 B2                                    Page 1 of 1
APPLICATION NO.    : 11/031973
DATED              : August 4, 2009
INVENTOR(S)        : Shawn Levy and Richard M. Caprioli It is certified that error appears in the above-identified patent and that said Letters Patent is hereby corrected as shown below:

In column 1, line 8, insert
--This invention was made with government support under Award No. W81XWH-04-1-0626 awarded by the U.S. Army Medical Research and Materiel Command. The government has certain rights in the invention.--.

Signed and Sealed this

Thirteenth Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,569,392 B2 Page 1 of 1
APPLICATION NO. : 11/031973
DATED : August 4, 2009
INVENTOR(S) : Levy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 912 days.

Signed and Sealed this

Seventh Day of September, 2010

David J. Kappos
*Director of the United States Patent and Trademark Office*